United States Patent
Pulé et al.

(10) Patent No.: US 11,578,126 B2
(45) Date of Patent: *Feb. 14, 2023

(54) CHIMERIC ANTIGEN RECEPTOR (CAR) COMPRISING A CD19-BINDING DOMAIN

(71) Applicant: AUTOLUS LIMITED, London (GB)

(72) Inventors: Martin Pulé, London (GB); Leila Mekkaoui, London (GB); Persis Amrolia, London (GB); Sara Ghorashian, London (GB); Anne Kramer, London (GB); Gordon Cheung, London (GB)

(73) Assignee: AUTOLUS LIMITED, London (GB)

( * ) Notice: Subject to any disclaimer, the term of this patent is extended or adjusted under 35 U.S.C. 154(b) by 662 days.

This patent is subject to a terminal disclaimer.

(21) Appl. No.: 16/573,854

(22) Filed: Sep. 17, 2019

(65) Prior Publication Data

US 2020/0140544 A1  May 7, 2020

Related U.S. Application Data

(63) Continuation of application No. 15/555,508, filed as application No. PCT/GB2016/050574 on Mar. 4, 2016, now Pat. No. 10,457,730.

(30) Foreign Application Priority Data

Mar. 5, 2015 (GB) ..................... 1503742

(51) Int. Cl.
| | |
|---|---|
| C07K 16/28 | (2006.01) |
| A61K 35/17 | (2015.01) |
| C07K 14/705 | (2006.01) |
| C07K 16/30 | (2006.01) |
| C07K 14/725 | (2006.01) |
| C12N 5/0783 | (2010.01) |

(52) U.S. Cl.
CPC .......... *C07K 16/2803* (2013.01); *A61K 35/17* (2013.01); *C07K 14/7051* (2013.01); *C07K 14/70517* (2013.01); *C07K 14/70521* (2013.01); *C07K 14/70578* (2013.01); *C07K 14/70596* (2013.01); *C07K 16/3061* (2013.01); *C12N 5/0636* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2319/03* (2013.01); *C07K 2319/33* (2013.01); *C07K 2319/74* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 10,098,926 B2 | 10/2018 | Pule et al. | |
| 10,174,099 B2 | 1/2019 | Pule et al. | |
| 10,457,730 B2* | 10/2019 | Pulé | A61P 35/02 |
| 2017/0369550 A1 | 12/2017 | Pule et al. | |
| 2018/0371054 A1 | 12/2018 | Pule et al. | |
| 2019/0161531 A1 | 5/2019 | Pule et al. | |

FOREIGN PATENT DOCUMENTS

| | | |
|---|---|---|
| CN | 102421800 A | 4/2012 |
| CN | 104159909 A | 11/2014 |
| WO | WO-2010/095031 A2 | 8/2010 |
| WO | WO-2013/126712 A1 | 8/2013 |
| WO | WO-2014/184143 A1 | 11/2014 |

OTHER PUBLICATIONS

Brentjens, et al., CD19-targeted T cells rapidly induce molecular remissions in adults with chemotherapy-refractory acute lymphoblastic leukemia, *Sci. Transl. Med.*, 5:177ra38 (2013).
Davila et al., Efficacy and Toxicity Management of 19-28z CAR T Cell Therapy in B Cell Acute Lymphoblastic Leukemia, *Sci. Translat. Med.*, 6:224RA24 (2014).
Day et al., PD-1 expression on HIV-specific T cells is associated with T-cell exhaustion and disease progression, *Nature*, 443:350-4 (2006).
EPO Communication Pursuant to Rule 161(1) and 162 EPC dated Oct. 17, 2017 in EP 16709529.8.
EPO Rule 71(3) Communication dated Nov. 9, 2018 in EP 16709529.8.
Ghorashian et al., A novel low affinity CD19CAR results in durable disease remissions and prolonged CAR T cell persistence without severe CRS or neurotoxicity in patients with paediatric ALL, *Blood*, 130(806):1-5 (2007).
Guedan et al., Enhancing CAR T cell persistence through ICOS and 4-1BB costimulation., *JCL Insight*, doi: 10.1172/jci.insight.96976 (2018).

(Continued)

*Primary Examiner* — James D Schultz
(74) *Attorney, Agent, or Firm* — Marshall, Gerstein & Borun LLP

(57) ABSTRACT

There is provided a chimeric antigen receptor (CAR) comprising a CD19-binding domain which comprises a) a heavy chain variable region (VH) having complementarity determining regions (CDRs) with the following sequences: CDR1—GY-AFSSS (SEQ ID No. 1); CDR2—YPGDED (SEQ ID No. 2) CDR3—SLLYGDYLDY (SEQ ID No. 3); and b) a light chain variable region (VL) having CDRs with the following sequences: CDR1—SASSSVSYMH (SEQ ID No. 4); CDR2—DTSKLAS (SEQ ID No. 5) CDR3—QQWNINPLT (SEQ ID No. 6). There is also provided a cell comprising such a CAR, and the use of such a cell in the treatment of cancer, in particular a B cell malignancy.

21 Claims, 11 Drawing Sheets

Specification includes a Sequence Listing.

(56) References Cited

OTHER PUBLICATIONS

Imai et al., Chimeric receptors with 4-1BB signaling capacity provoke potent cytotoxicity against acute lymphoblastic leukemia, *Leuk.*, 18:676-84 (2004).
International Preliminary Reporton Patentability, PCT/GB2016/050574 (dated Sep. 5, 2017).
International Search Report and Written Opinion for PCT/GB2016/050574 (dated May 20, 2016).
Kochenderfer et al., Chemotherapy-Refractory Diffuse Large B-Cell Lymphoma and Indolent B-Cell Malignancies., *J. Clin Oncol.*, 33:540-549 (2015).
Lee et al., T cells expressing CD19 chimeric antigen receptors for acute lymphoblastic leukaemia in children and young adults: a phase 1 dose-escalation trial, *Lancets*, 385(9967):517-28 (2015).
Lichtman et al., Chimeric Antigen receptor T-Cells for B-Cell malignancies, *Trans. Res.*, 187:59-82 (2017).
Long et al., 4-1BB costimulation ameliorates T cell exhaustion induced by tonic signaling of chimeric antigen receptors, *Nature Med.*, 21(6):581-90 (2015).
López-Alvarez et al., Association of monoclonal expansion of Epstein-Barr virus-negative CD158a+ NK cells secreting large amounts of gamma interferon with hemophagocytic lymphohistiocytosis, *Clin. Vaccine Immunol.*, 16(1):142-5 (2009).
Maude et al., Chimeric Antigen Receptor T Cells for Sustained Remissions in Leukemia, *New Engl. J. Med.*, 371:1507-1517 (2014).
Qasim et al., Preliminary results for UCART19, an allogenic antiCD19 CAR T-cell product in a first-in-human trial (PALL) in pediatric patients with CD19+ relapsed/refractory B-cell acute lymphoblastic leukemia, *Blood*, 130(127):1-4 (2017).
Amrolia P.J., et al., "Chimeric Antigen Receptor T Cells for ALL," Lancet, Feb. 7, 2015, vol. 385, pp. 488-490.
Kochenderfer et al., Construction and Pre-clinical Evaluation of an Anti-CD19 Chimeric Antigen Receptor, J. Immunother., 2009, vol. 32, No. 7, pp. 689-702.

\* cited by examiner (b)

| Query protein sequence | Q | I | V | L | T | Q | S | P | A | I | M | S | A | S | P | G | E | K | V | T |
|---|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |

CHOTHIA REGIONS | LFR1

| M | T | C | S | A | S | S | S | V | S | Y | M | H | W | Y | Q | Q | K | S | G | T | S | P |
|---|---|---|---|---|---|---|---|---|---|---|---|---|---|---|---|---|---|---|---|---|---|---|
| L21 | L22 | L23 | L24 | L25 | L26 | L27 | L28 | L29 | L30 | L32 | L33 | L34 | L35 | L36 | L37 | L38 | L39 | L40 | L41 | L42 | L43 | L44 |

CDR-L1 | LFR2

| K | R | W | I | Y | D | T | S | K | L | A | S | G | V | P | D | R | F | S | G | S | G | S |
|---|---|---|---|---|---|---|---|---|---|---|---|---|---|---|---|---|---|---|---|---|---|---|
| L45 | L46 | L47 | L48 | L49 | L50 | L51 | L52 | L53 | L54 | L55 | L56 | L57 | L58 | L59 | L60 | L61 | L62 | L63 | L64 | L65 | L66 | L67 |

CDR-L2 | LFR3

| G | T | S | Y | F | L | T | I | N | N | M | E | A | E | D | A | A | T | Y | Y | C | Q | Q |
|---|---|---|---|---|---|---|---|---|---|---|---|---|---|---|---|---|---|---|---|---|---|---|
| L68 | L69 | L70 | L71 | L72 | L73 | L74 | L75 | L76 | L77 | L78 | L79 | L80 | L81 | L82 | L83 | L84 | L85 | L86 | L87 | L88 | L89 | L90 |

⇧ | CDR-L3

| W | N | I | N | P | L | T | F | G | A | G | T | K | L | E | L | K | R |
|---|---|---|---|---|---|---|---|---|---|---|---|---|---|---|---|---|---|
| L91 | L92 | L93 | L94 | L95 | L96 | L97 | L98 | L99 | L100 | L101 | L102 | L103 | L104 | L105 | L106 | L107 | L108 |

⇧ | LFR4

⇧ Unusual residue (<1% of sequences)

CHIMERIC ANTIGEN RECEPTOR (CAR) COMPRISING A CD19-BINDING DOMAIN

CROSS-REFERENCE TO RELATED APPLICATIONS

This application is a continuation of U.S. application Ser. No. 15/555,508, filed on Sep. 3, 2017. U.S. application Ser. No. 15/555,508 is a National Stage of International Application No. PCT/GB2016/050574, filed on Mar. 4, 2016, and claims the benefit of priority to GB Application No. 1503742.7, filed on Mar. 5, 2015, all of which are hereby incorporated by referenced in their entireties for all purposes.

SEQUENCE LISTING

The instant application contains a Sequence Listing which has been submitted electronically in ASCII format and is hereby incorporated by reference in its entirety. Said ASCII copy was created on Sep. 17, 2019, is named 52309A_Seqlisting.txt and is 66,371 bytes in size.

FIELD OF THE INVENTION

The present invention relates to a chimeric antigen receptor (CAR) which binds the B-lymphocyte antigen CD19 (Cluster of Differentiation 19). T cells expressing such a CAR are useful in the treatment of cancerous diseases such as B-cell leukemias and lymphomas.

BACKGROUND TO THE INVENTION

Chimeric Antigen Receptors

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords us a solution to this problem: transgenic expression of Chimeric Antigen Receptor (CAR) allows large numbers of T-cells specific to any surface antigen to be easily generated by ex vivo viral vector transduction of a bulk population of peripheral blood T-cells.

The most common forms of these molecules are fusions of single-chain variable fragments (scFv) derived from monoclonal antibodies which recognise a target antigen, fused via a spacer and a transmembrane domain to a signalling endodomain. Such molecules result in activation of the T-cell in response to recognition by the scFv of its cognate target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers. To-date however, the main clinical exploration and potential application of CAR therapy is as treatment for B-cell malignancies.

CARs Directed Against CD19

CD19 is a B-cell antigen which is expressed very early in B-cell differentiation and is only lost at terminal B-cell differentiation into plasma cells. Hence, CD19 is expressed on all B-cell malignancies apart from multiple myeloma. It is not expressed on other haematopoietic populations or non-haematopoietic cells and therefore targeting this antigen should not lead to toxicity to the bone marrow or non-haematopoietic organs. Loss of the normal B-cell compartment is considered an acceptable toxicity when treating lymphoid malignancies, because although effective CD19 CAR T cell therapy will result in B cell aplasia, the consequent hypogammaglobulinaemia can be treated with pooled immunoglobulin.

CD19 is therefore an attractive CAR target. To date, the main clinical focus of the CAR field has been studies targeting CD19 on refractory B-cell cancers, as summarised in Table 1.

Different designs of CARs have been tested against CD19 in different centres, as outlined in Table 1:

TABLE 1

Summary of CAR experience targeting CD19

| Centre | Binder | Endodomain | Comment |
| --- | --- | --- | --- |
| University College London | Fmc63 | CD3-Zeta | Low-level brief persistence |
| Memorial Sloane Kettering | SJ25C1 | CD28-Zeta | Short-term persistence |
| NCI/KITE | Fmc63 | CD28-Zeta | Long-term low-level persistence |
| Baylor, Centre for Cell and Gene Therapy | Fmc63 | CD3-Zeta/ CD28-Zeta | Short-term low-level persistence |
| UPENN/Novartis | Fmc63 | 41BB-Zeta | Long-term high-level persistence |

Most of the studies have tested CD19 CARs based on a scFv derived from the hybridoma fmc63. The most promising have been in the treatment of Acute Lymphoblastic Leukaemia (ALL).

Clinical Experience with CARs Against CD19

CD19 directed CAR therapy appears most effective in ALL. The first studies in ALL were published in Spring 2013, by groups from Memorial Sloane Kettering (Brentjens, et al. (2013) Leukemia. Sci. Transl. Med. 5, 177ra38) and the University of Pennsylvania. An update report of the latter study has recently been made (Maude et al. (2014) N. Engl. J. Med. 371, 1507-1517). Here, 25 patients under the age of 25 years and 5 over this age were treated. 90% achieved a complete response at one month, 22 of 28 evaluable cases achieved an MRD negative status and the 6 month event free survival rate was 67%. 15 patients received no further therapy after the study.

Brentjens et al., (as above) in the adult setting, treated 5 ALL patients (2 with refractory relapse, 2 with MRD positive disease and 1 who was MRD negative) with autologous T cells retrovirally transduced to express a CD19 CAR incorporating an scFv derived from the SJ25C1 hybridoma and a CD28 co-stimulatory domain. All of these achieved a deep molecular remission, enabling 4 of these patients to receive an allogeneic SCT. This precluded assessment of the durability of responses but CAR T cells were only detectable in the blood or bone marrow for 3-8 weeks after infusion. The patient who was not transplanted relapsed at 90 days with CD19+ disease. Subsequently, Davila et al. ((2014). Sci. Transl. Med. 6, 224ra25) have updated this cohort. 14 of 16 adult patients had detectable disease at the point of CAR T cell infusion, despite salvage chemotherapy and cyclophosphamide conditioning. 14 of 16 achieved a complete remission with or without count recovery including 7 of 9 patients with morphologic evidence of residual disease detectable after salvage chemotherapy. 12 of 16 patients achieved MRD negativity and this allowed 7 to undergo allogeneic transplantation by the time of publication. Responses were durable in some patients with 4 of 8 non-transplanted patients continuing in morphological remission at up to 24 months follow-up although the survival curves for this cohort are not yet stable.

A recently published study in a cohort of paediatric and young adult patients predominantly with ALL provides the first intention-to-treat analysis of its outcomes. This may help remove the bias inherent in excluding patients who do not receive the anticipated dose of CAR T cells (Lee et al. (2014) Lancet. doi:10.1016/S0140-6736(14)61403-3). 21 patients were treated with a CD28 domain-containing second generation CAR. All but 2 patients received the anticipated T cell dose, highlighting the feasibility of delivering this treatment to those with refractory or multiply-relapsed ALL. This study shows the following efficacy: 67% achieving a complete remission and 60% of those with ALL achieving MRD negative status.

Immune Toxicity of CD19 CAR Therapy

Cytokine release syndrome (CRS) encompasses a range of inflammatory symptoms ranging from mild to multi-organ failure with hypotension and respiratory failure. Some degree of CRS occurs commonly in patients treated with CD19 CAR T cells. Approximately 30% (21/73) patients treated in recent cohorts showed some degree of CRS (Davilia et al (2014) as above; Lee et al (2014) as above; Kochenderfer (2014) J. Clin. Oncol. Off. J. Am. Soc. Clin. Oncol. doi:10.1200/JCO.2014.56.2025). CRS has also been seen in patients treated with blinatumomab, a bi-specific recombinant single-chain antibody recognising both CD19 and CD3. CRS typically occurs 5-21 days after CAR T cell infusion.

CRS can be life threatening and requires treatment in an intensive care setting. CRS is associated with elevated serum cytokine levels. The cytokines most significantly elevated are IL-6, IL-10 and interferon gamma (IFNγ). Clinical manifestations of severe CRS (fever, hepatosplenomegaly, coagulopathy and hyperferritinaemia) resemble macrophage activation syndrome (MAS) found for instance in patients with congenital defects in T-cells. This suggests that common immunopathological processes are involved. At present it is not clear which cell type (CAR T cells, dying tumour cells, or locally-activated macrophages) are responsible for production of the key cytokines, particularly IL-6. However, a key initiating factor in MAS is release of copious Interferon-gamma (López-Alvarez et al. (2009). Clin. Vaccine Immunol. CVI 16, 142-145).

Neurotoxicity

A number of patients in CD19 CAR studies across institutions have developed transient neurotoxicity with a spectrum of severity from aphasia to obtundation, delirium and seizures (Davilia et al (2014) as above). This appears to be restricted to patients with ALL and a similar syndrome has been documented after blinatumomab therapy. Brain imaging appears normal. Neurotoxicity may reflect high levels of systemic cytokines crossing the blood-brain barrier.

Persistence, Relapse and T-Cell Exhaustion

Durable responses appeared to correlate with higher peak levels of circulating CAR transduced T cells, as well as with the duration of B cell aplasia. With exception of patients relapsing with CD19− disease, relapse was generally associated with loss of circulating CAR T cells and recovery of normal B cells.

T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. Recently, a clearer picture of the functional and phenotypic profile of exhausted T cells has emerged with expression of inhibitory receptor programmed death 1 (PD-1; also known as PDCD1), a negative regulator of activated T cells, being a key feature (Day et al. (2006) Nature 443, 350-354).

Responses in CD19 CAR studies suggest that persistence of T-cells for a protracted period at high levels seems to be important in effecting durable responses. A CD19 CAR which reduces T-cell exhaustion may result in improved clinical responses.

There is thus a need for an alternative CAR directed against CD19 which is not associated with the above disadvantages.

Sequences of the VH and VL are numbered using Chothia numbering. The framework and CDR regions are shown. Insertions are also shown.

Figure 1:
FIG. 1. Annotated and numbered (a) CAT19 VH sequences; (b) CAT19 VL
Figure 2:
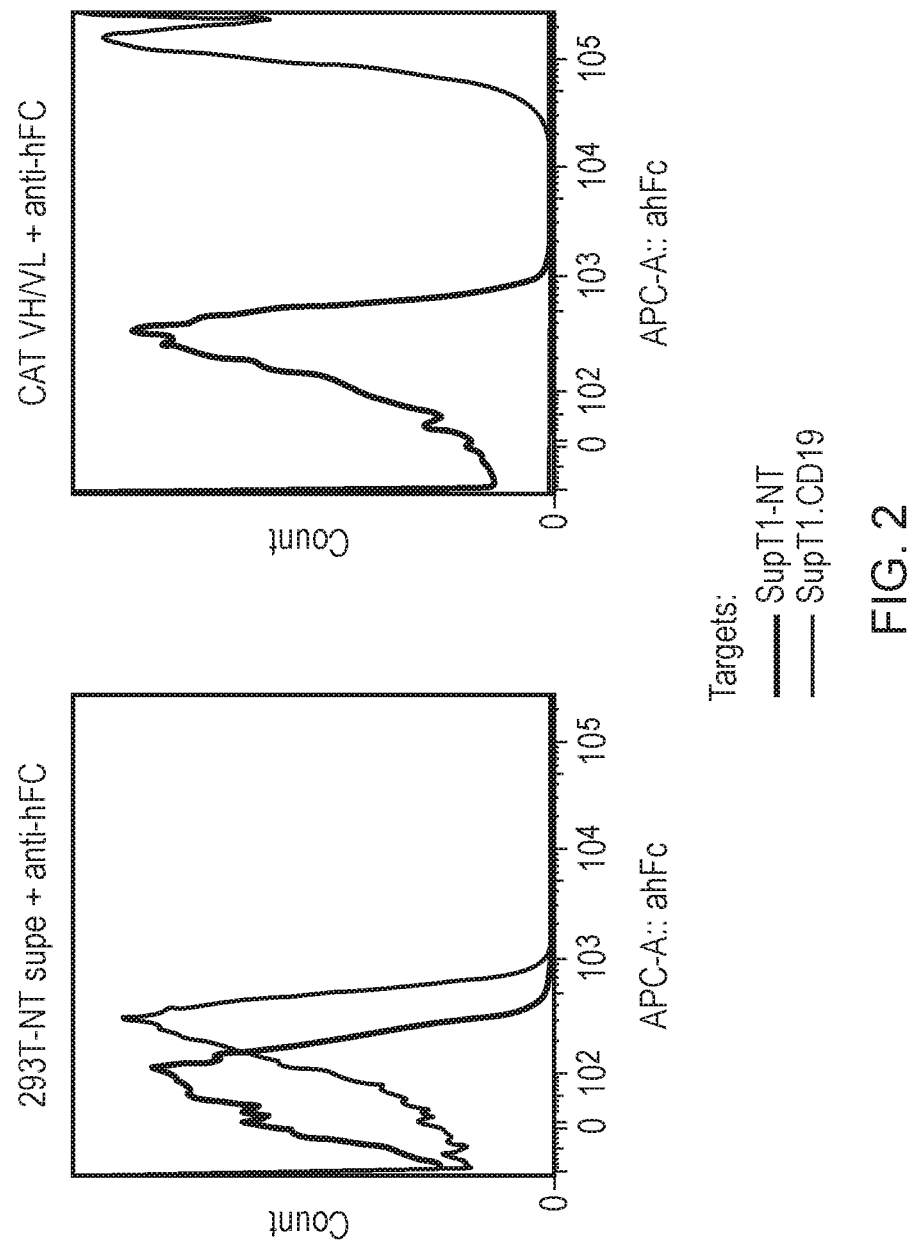

FIG. 2. Staining of CD19 positive cells with recombinant CAT19

SupT1 cells do not normally express CD19 but were engineered to do so in this study. CAT19 VH and VL sequences were cloned into mouse IgG2a heavy chain format and mouse kappa light chain format, both in mammalian expression plasmids. 293T cells were transfected simultaneously with both heavy and light chain and the resultant antibody purified with protein A. SupT1 cells and SupT1.CD19 cells were stained with this recombinant antibody (or plain 293T supernatant) and further stained with a fluorescently conjugated anti-mouse secondary. Binding of recombinant CAT19 antibody could readily be detected by flow-cytometry.

Figure 3:
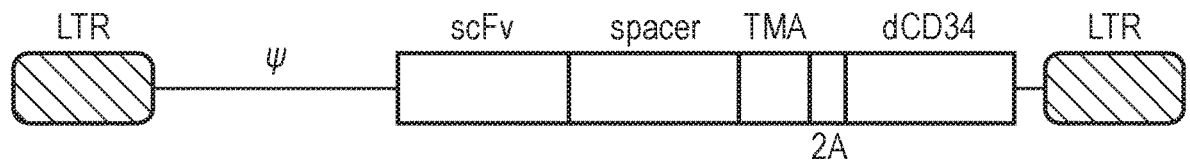
Figure 3:
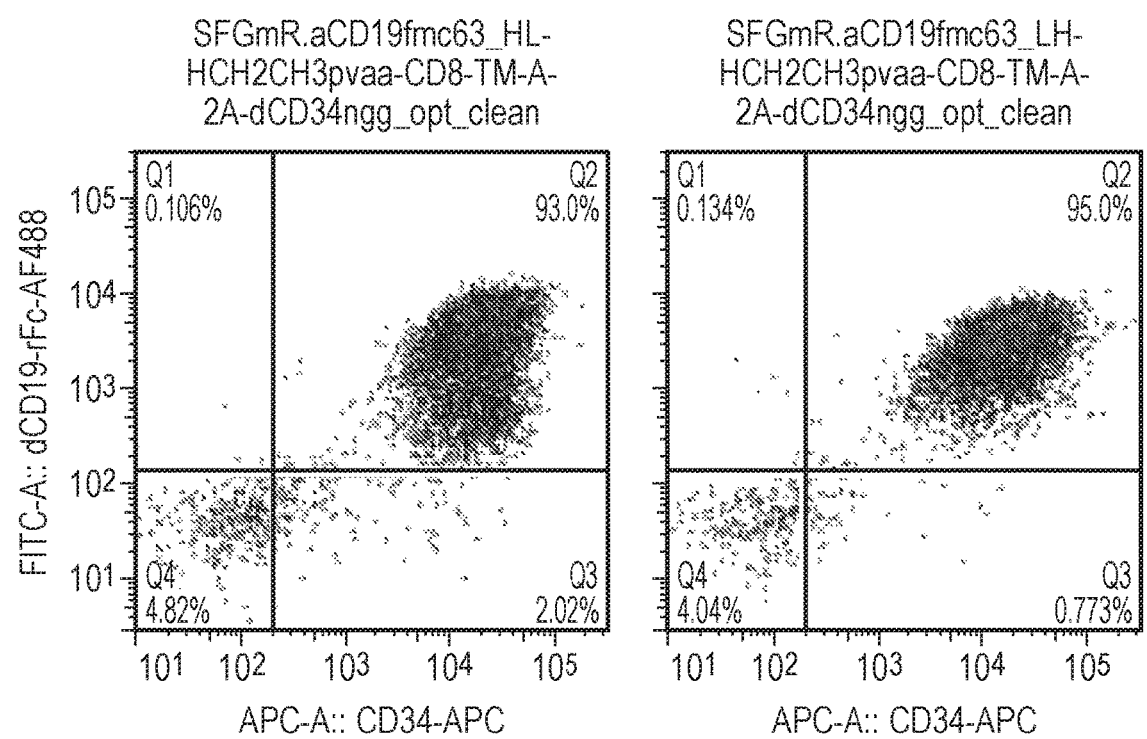
Figure 3:
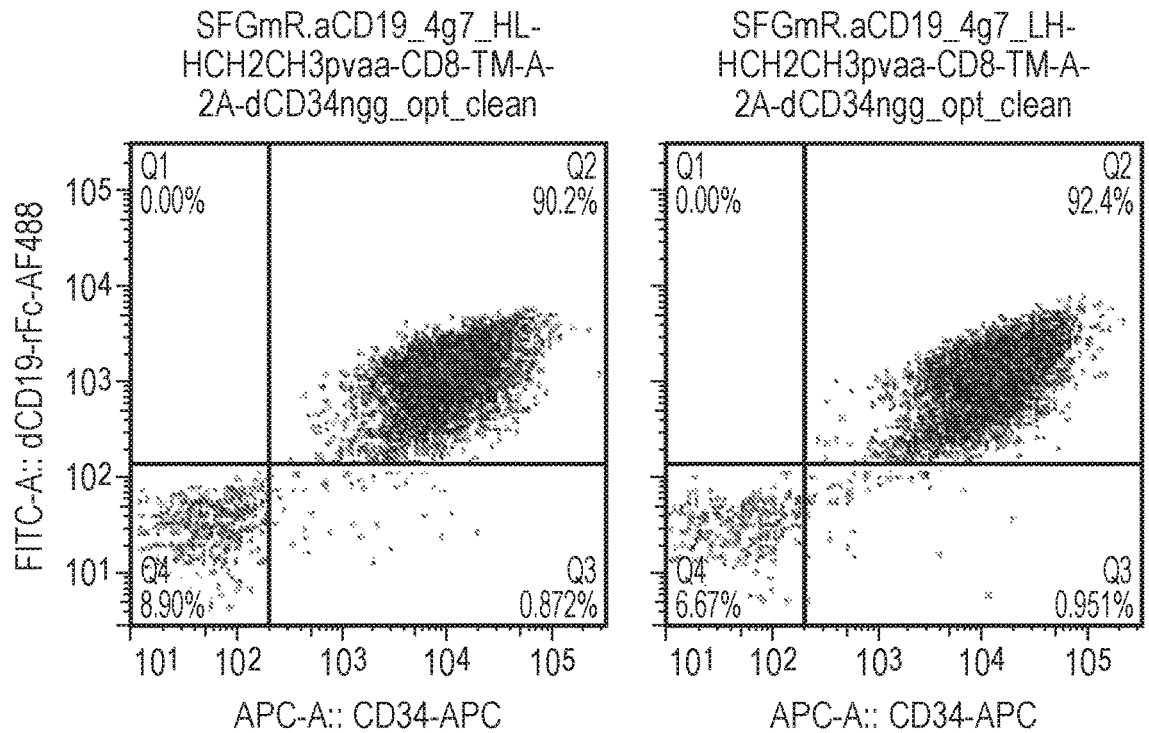
Figure 3:
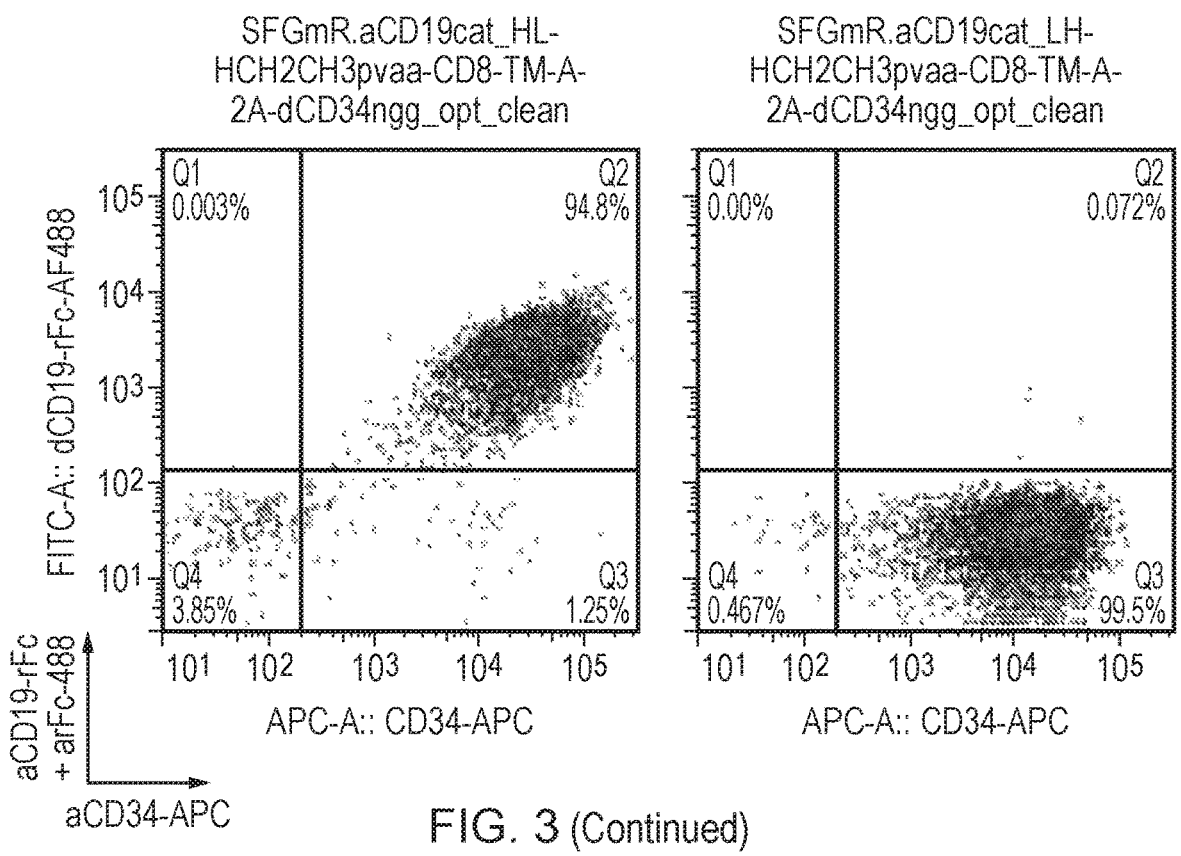

FIG. 3. Staining of CD19 positive cells with CAT19 scFv

The VH and VL of CAT19 were cloned such that they form a scFv whereby the VH and VL are separated by a $(SGGGGS)_3$ linker. Two scFvs were generated with the CAT scFv in both VH-VL and VL-VH orientations. In addition, scFvs were generated, also in either orientation, from the anti-CD19 antibodies fmc63 and 4g7. (a) scFv display format: this is a retroviral vector whereby the scFv is cloned onto a human IgG1 Fc spacer which has the CD8 transmembrane domain and the first 12 residues of the CD8 endodomain. This in turn is in frame with the FMD-2A peptide TaV and truncated human CD34. In this way, the scFv is displayed on the surface of a cell, and the transgene expression can be controlled for by detecting CD34 separately. SupT1 cells were generated which express either of the 6 different scFv formats and these cells were stained with recombinant human truncated CD19-mouse IgG2a Fc fusion and anti-CD34; (b) Staining with fmc63 VH-VL and VL-VH format; (c) Staining with 4g7 VH-VL and VL-VH format; and (d) Staining with CAT19 VH-VL and VL-VH format. Surprisingly, the CAT19 VH-VL scFv bound well, while the VL-VH scFv gave significantly less detectable binding.

Figure 4:
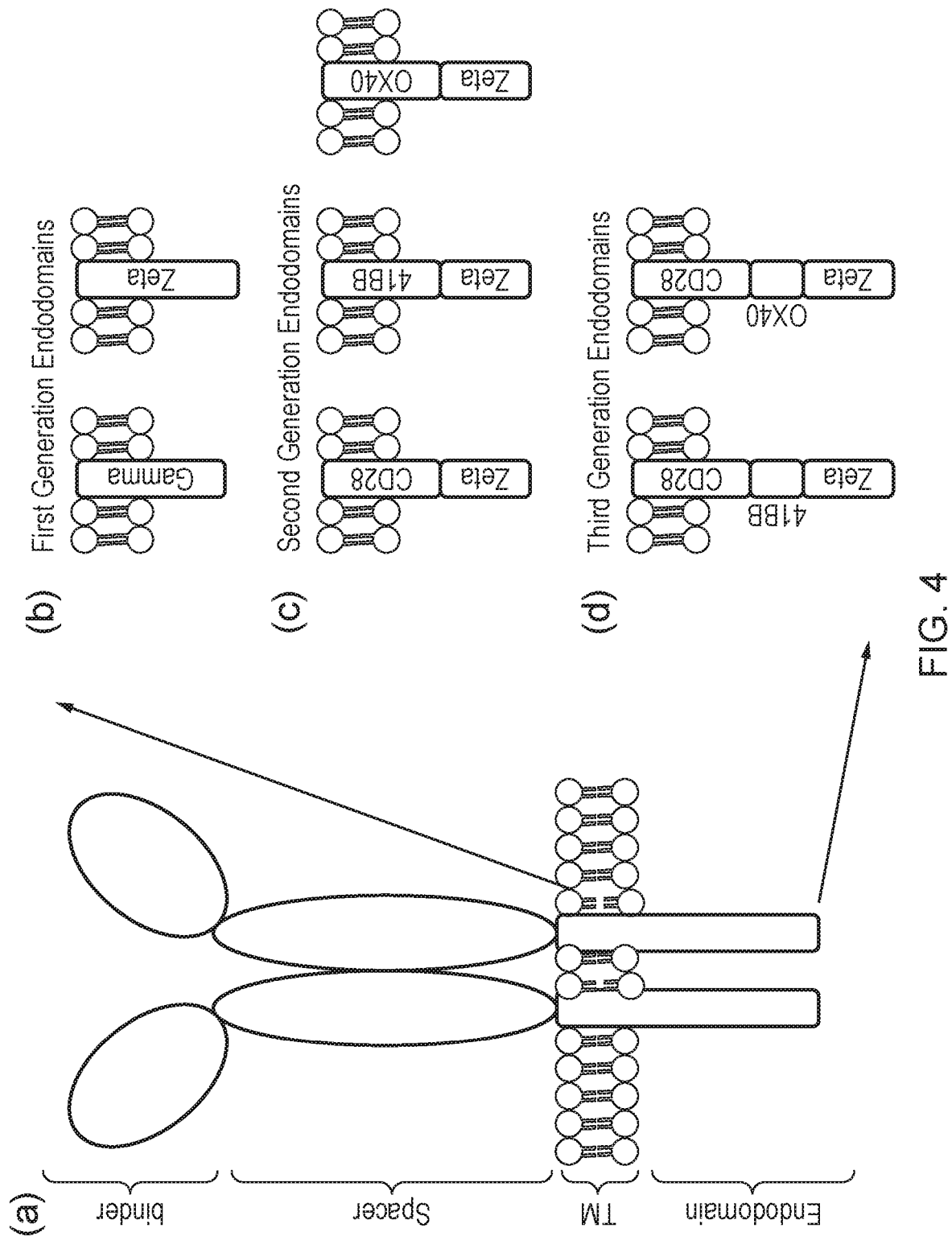
Figure 4:
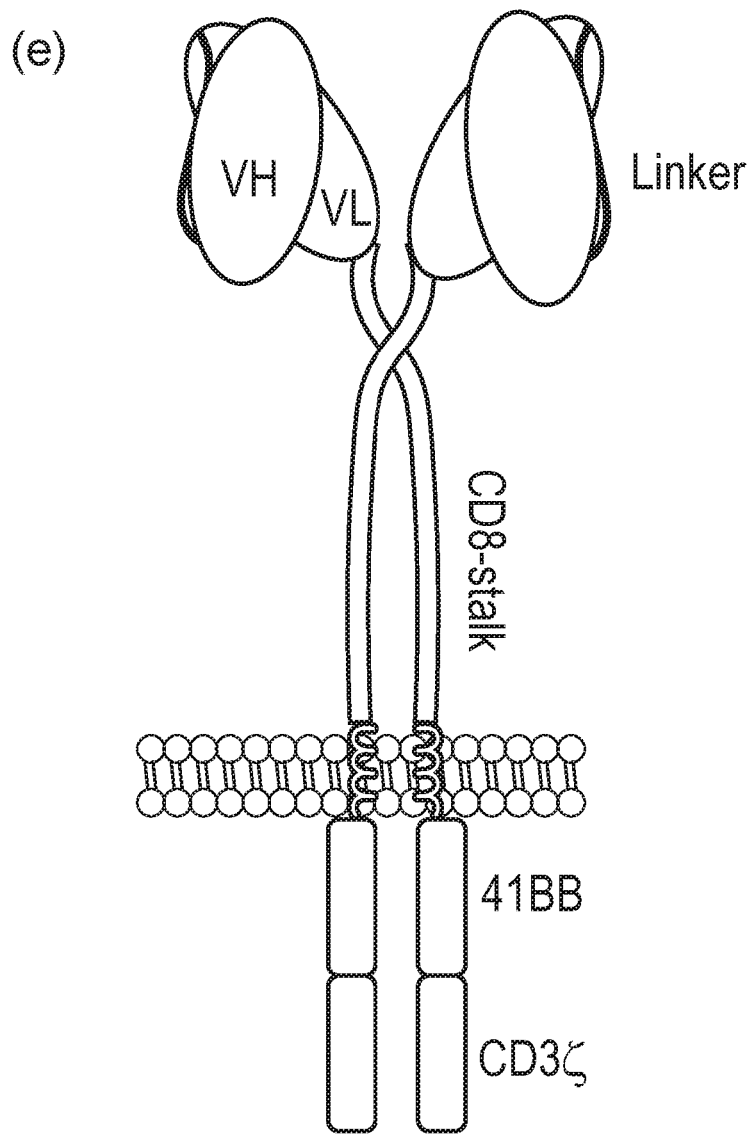

FIG. 4. Different generations of CARs and initial CARs tested (a) A typical CAR format comprising of an antigen binding domain (which most usually is a scFv), a spacer domain, a transmembrane domain and one or several signalling domains. (b) First generation CARs transmit an activation signal; their endodomain is derived from either the FcGamma receptor endodomain or the CD3 Zeta endodomain; (c) Second generation receptors transmit two signals: their endodomains comprise a co-stimulatory domain connected to the endodomain of CD3-Zeta. The co-stimulatory domain is usually either the endodomain of CD28, the endodomain of OX40 or the endodomain of 41BB. (d) Third generation receptors transmit three signals: their endodomains comprise a fusion of the CD28 endodomain with the 41BB endodomain and with the CD3-Zeta endodomain, or the CD28 endodomain with the OX40 endodomain and with the CD3-Zeta endodomain. (e) The CAT19 based CAR initially tested which comprises a scFv in the VH-VL orientation, a CD8 stalk spacer and $2^{nd}$ generation endodomain comprising of 41BB-Zeta (Campana CAR format).

Figure 5:
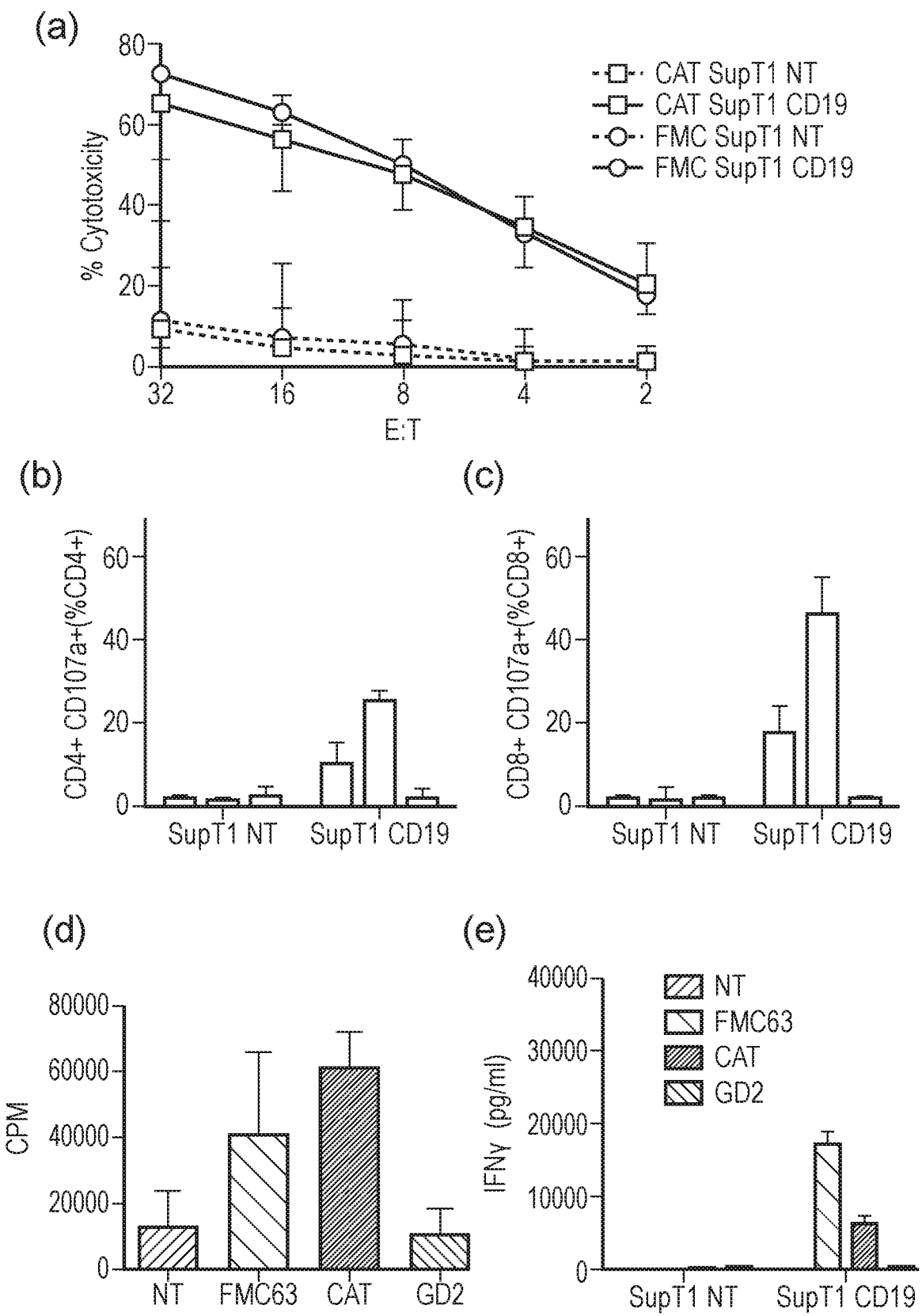

FIG. 5. In vitro comparison of CAT19 CAR function against fmc36 CAR

Primary human T-cells from 5 different donors were transduced with lentiviral vectors coding for CAT19 CAR in Campana format, or the Campana CAR itself. These T-cells were then used in various assays. (a) Chromium release assay was performed against SupT1 cells. These cells are CD19 negative. Neither CAR T-cells responded against this cell line (dotted lines). Chromium release assay was performed against SupT1.CD9. Both CARs performed equally against this cell line (unbroken lines). Next a degranulation assay was performed using either NT T-cells, fmc63 CAR T-cells, or CAT19 CAR T-cells against either SupT1 or SupT1.CD19. (b) data gated on CD4+ T-cells, and (c) CD8+ T-cells is shown. Degranulation was increased with CAR19 CAR T-cells. (d) Proliferation was estimated using tritiated thymidilation incorporation. NT, fmc63 CAR T-cells, CAT19 CAR T-cells were tested against SupT1. CD19. In this experiment, an irrelevant CAR targeting GD2 was also tested. There was a trend to increased proliferation with CAR19 CAR T-cells. (e) Interferon-gamma release from either NT T-cells, fmc63 CAR T-cells, CAT19 CAR T-cells or GD2 CAR T-cells 24 hours after challenge against SupT1 or SupT1.CD19 cells. CAT19 CAR T-cells produced significantly less IF-G than fmc63 CAR T-cells when challenged with CD19+ targets.

Figure 6:
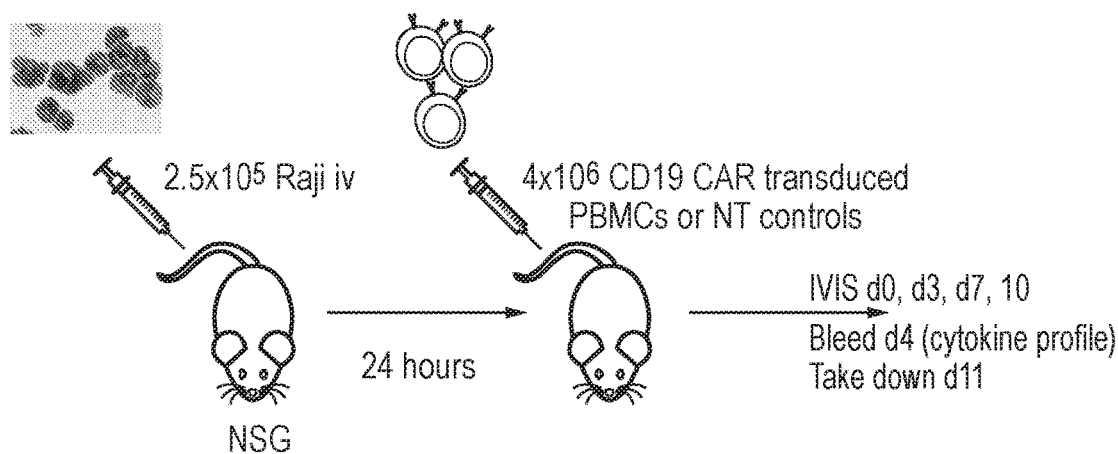
Figure 6:
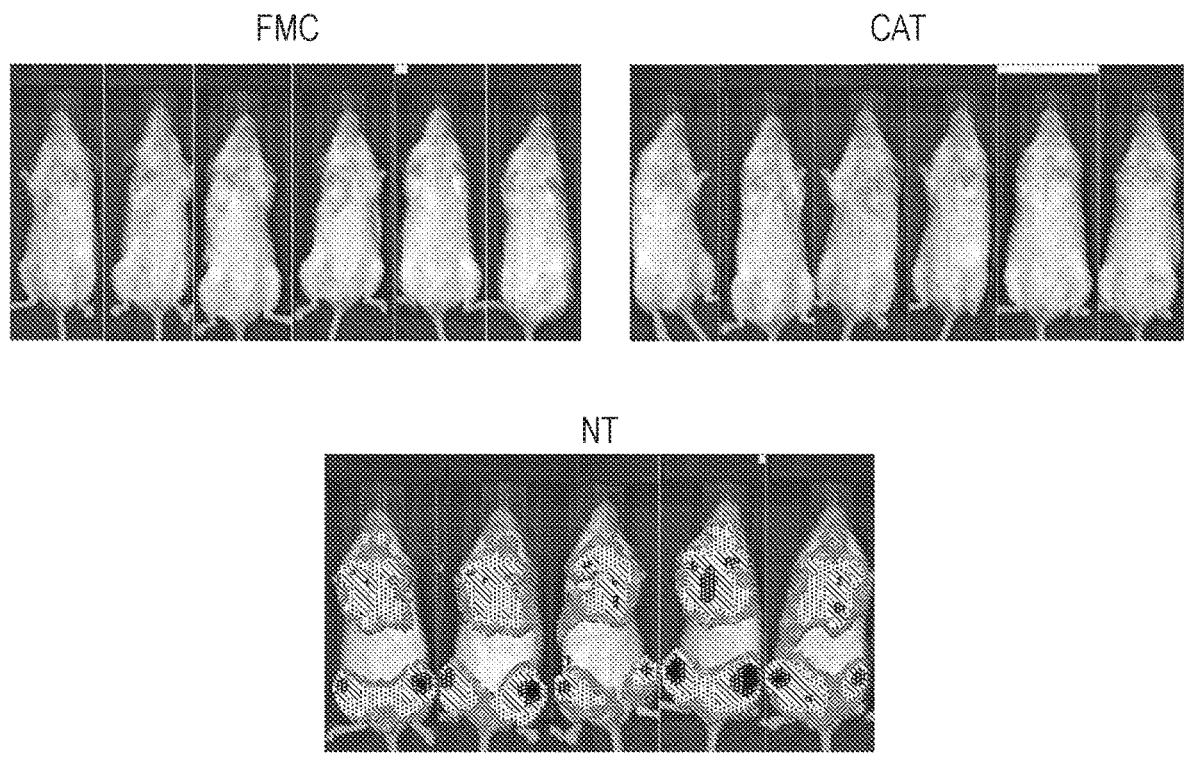
Figure 6:
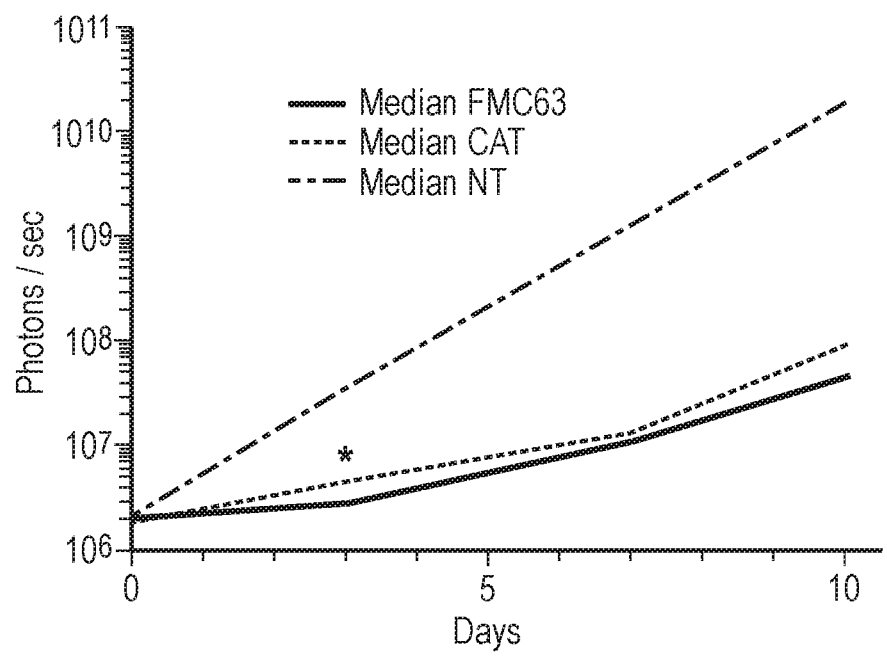
Figure 6:
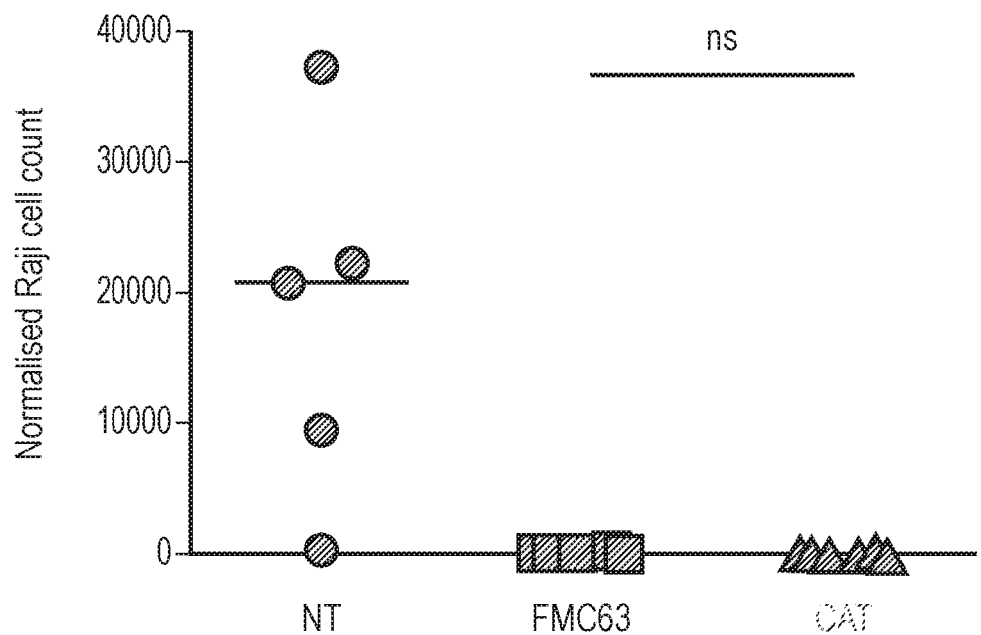

FIG. 6. In vivo model of CAT19 efficacy.

(a) Outline of experimental set-up for in vivo model. NSG mice were injected with 2.5×10^5 Raji.FLuc cells via tail vein injection. 24 hours later 4×10^6 of either NT primary human T-cells, or T-cells transduced with fmc63 CAR, or T-cells transduced with CAT19 CAR were administered via tail-vein. Tumour response was measured sequentially by bioluminescence imaging. Tail-vein blood was sampled at day 4 for engraftment and serum cytokine. The animals were culled at day 11 and tissues studied for persistence of CAR T-cells and tumour burden. (b) Bioluminescence imaging of the different mouse cohorts at day 10. Extensive disease is seen in the pelvis, spine, ribs, skull and spleen of mice treated with NT T-cells, while minimal signal is evident in mice who received either CAT19 CAR T-cells, or fmc63 CAR T-cells. (c) Quantitative bioluminescent signal averaged from different mouse cohorts over time. Y-axis is a log-scale; A clear difference is seen between signal accumulation in mice who received NT T-cells, and mice who received CAR T-cells. No difference in signal accumulation is seen in mice who received fmc63 CAR T-cells or CAT19 CAR T-cells. (d) Flow-cytometric determined tumour burden in bone-marrow from mice at the end of the experiment. Practically no Raji cells could be detected in marrow of mice who received either fmc63 CAR or CAT19 CAR T-cells.

Figure 7:
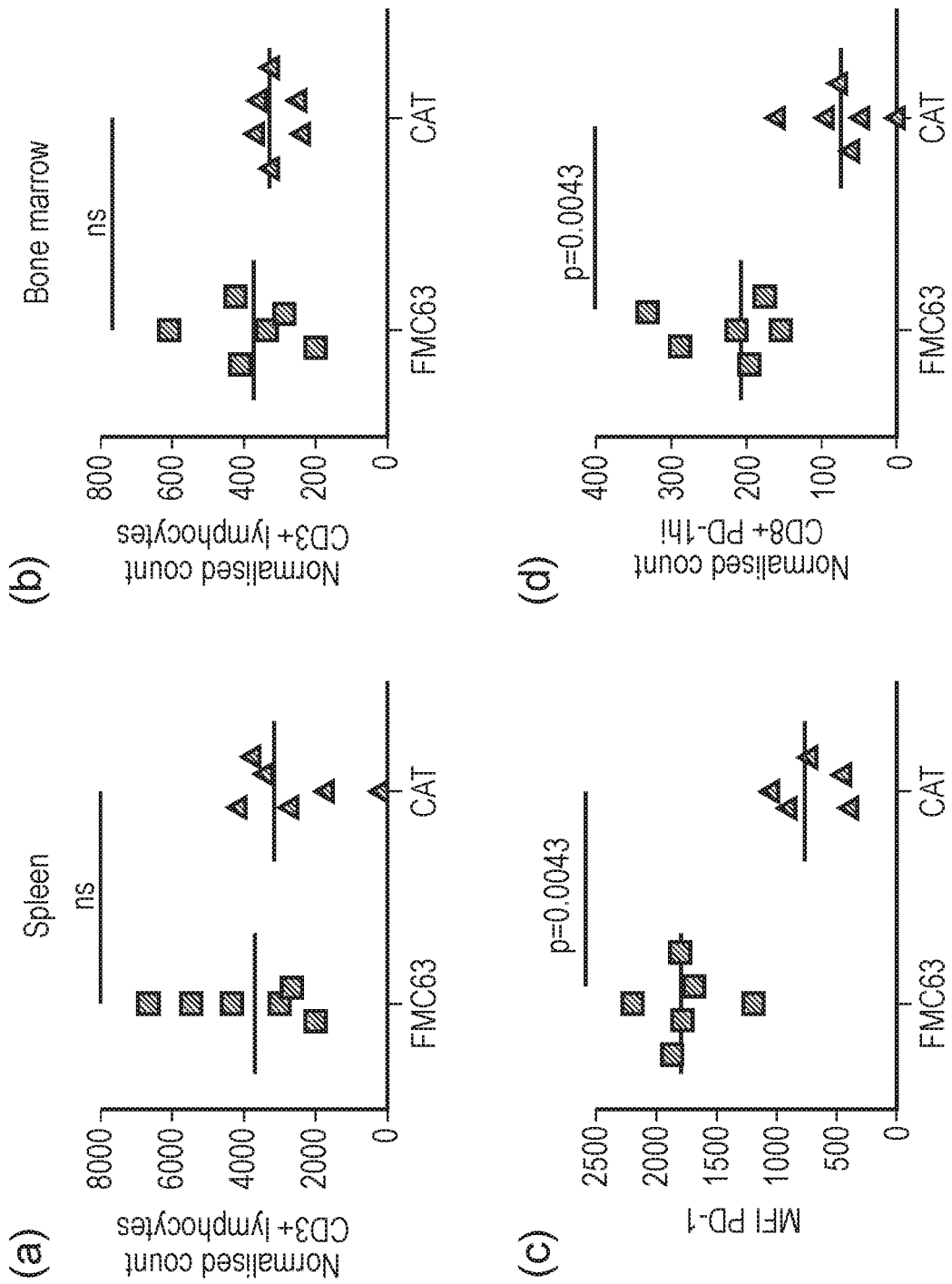

FIG. 7. Characterization of in vivo persisting CAR T-cells (a) Absolute numbers of CAR T-cells in spleens of mice from animals treated with fmc63 CAR T-cells or CAT19 CAR T-cells in the model outlined above. This shows the same numbers are present in both; (b) Absolute numbers of CAR T-cells in bone-marrow of mice treated with fmc63 CAR T-cells or CAT19 CAR T-cells. This shows the same numbers of cells are present in both; (c) Absolute numbers of PD1-expressing CAR T-cells in spleen and (d) bone-marrow of mice treated with either fmc63 CAR T-cells or CAT19 CAR T-cells. Fewer of the CAT19 T-cells are PD1+ in both compartments.

SUMMARY OF ASPECTS OF THE INVENTION

The present inventors have developed a new CD19-specific CAR with CDRs that have not previously been described. It has equivalent potency to the fmc63-based CAR used in the UPENN studies, but results in reduced toxicity and reduced T-cell exhaustion.

Thus, in a first aspect the present invention provides a chimeric antigen receptor (CAR) comprising a CD19-binding domain which comprises a) a heavy chain variable region (VH) having complementarity determining regions (CDRs) with the following sequences:

```
CDR1-
                                   (SEQ ID No. 1)
GYAFSSS;

CDR2-
                                   (SEQ ID No. 2)
YPGDED

CDR3-
                                   (SEQ ID No. 3)
SLLYGDYLDY;
``` b) a light chain variable region (VL) having CDRs with the following sequences:

```
CDR1-
                                   (SEQ ID No. 4)
SASSSVSYMH;

CDR2-
                                   (SEQ ID No. 5)
DTSKLAS

CDR3-
                                   (SEQ ID No. 6)
QQWNINPLT.
```

The CD19 binding domain may comprise a VH domain having the sequence shown as SEQ ID No. 7 and/or or a VL domain having the sequence shown as SEQ ID No 8 or a variant thereof having at least 95% sequence identity.

The CD19 binding domain may comprise an scFv in the orientation VH-VL.

The CD19 binding domain may comprise the sequence shown as SEQ ID No 9 or a variant thereof having at least 90% sequence identity.

The CD19 binding domain may comprise the 6 CDRs defined in claim 1 grafted on to a human antibody framework.

The CD19-binding domain and the transmembrane domain may be connected by a spacer, which may comprise one of the following: a human an IgG1 Fc domain; an IgG1 hinge; or a CD8 stalk. The spacer may comprise a CD8 stalk.

The CAR may comprise or associate with an intracellular T cell signalling domain.

The intracellular T cell signalling domain may comprise one or more of the following endodomains: CD28 endodomain; 41BB endodomain, OX40 endodomain and the CD3-Zeta endodomain.

In particular the CAR may comprise a CD8 stalk spacer and an intracellular T-cell signalling domain which comprises the 41BB endodomain and the CD3-Zeta endodomain.

In particular the CAR may comprise a CD8 stalk spacer and an intracellular T-cell signalling domain which comprises the OX40 endodomain and the CD3-Zeta endodomain.

In an alternative embodiment, the intracellular T cell signalling domain may comprise all of the following endodomains: CD28 endodomain; OX40 and CD3-Zeta endodomain.

The CAR may comprise the sequence shown as any of SEQ ID No. 10 to 15 or a variant thereof which has at least 80% sequence identity but retains the capacity to i) bind CD19 and ii) induce T cell signalling. The CAR may have advantageous properties compared to the fmc63-based CAR used in the UPENN studies. For example, the CAR, when expressed by a T-cell and used to target a CD19 expressing cell, may cause lower IFNγ release by the CD19-expressing target cell than that caused by a T-cell expressing a CAR comprising a CD19-binding domain which comprises: a) a heavy chain variable region (VH) having complementarity determining regions (CDRs) with the following sequences: CDR1—GVSLPDY (SEQ ID No. 16); CDR2—WGSET (SEQ ID No. 17); CDR3—HYYYGGSYAMDY (SEQ ID No. 18); and b) a light chain variable region (VL) having CDRs with the following sequences: CDR1—RASQDISKYLN (SEQ ID No. 19); CDR2—HTSRLHS (SEQ ID No. 20) CDR3—QQGNTLPYT (SEQ ID No. 21). The CDRs may be grafted on to a human or humanised framework.

In a second aspect, the present invention provides a nucleic acid sequence which encodes a CAR according to the first aspect of the invention.

In a third aspect, there is provided a vector which comprises a nucleic acid sequence according to the second aspect of the invention.

In a third aspect there is provided a cell which comprises a CAR according to the first aspect of the invention.

The cell may be a cytolytic immune cell, such as a T cell or a natural killer (NK) cell.

In a fourth aspect there is provided a cell composition which comprises a plurality of cells according to the third aspect of the invention.

In a fifth aspect, there is provided a method for making a cell according to the third aspect of the invention, which comprises the step of transducing or transfecting a cell with a vector according to the third aspect of the invention.

In a sixth aspect there is provided a method for making a cell composition according to the fourth aspect of the invention which comprises the step of transducing or transfecting a sample of cells from a subject ex vivo with a vector according to the third aspect of the invention.

The sample of cells may, for example, be a blood sample or a derivative thereof, such as a peripheral blood mononuclear cell (PBMC) sample.

In a seventh aspect, there is provided a pharmaceutical composition which comprises a cell according to the first aspect of the invention, or a cell composition according to the fourth aspect of the invention, together with a pharmaceutically acceptable carrier, diluent or excipient.

In an eighth aspect, there is provided a method for treating cancer which comprises the step of administering a cell according to the first aspect of the invention, a cell composition according to the fourth aspect of the invention or a pharmaceutical composition according to the seventh aspect of the invention to a subject.

The method may comprise the step of transducing or transfecting cells from the subject ex vivo with a vector according to the third aspect of the invention, then administering the, or some of the, transfected cells back to the subject.

There is also provided a pharmaceutical composition according to the seventh aspect of the invention for use in treating cancer.

There is also provided the use of a cell according to the third aspect of the invention in the manufacture of a pharmaceutical composition for treating cancer.

The cancer may, for example, be a B cell malignancy.

DETAILED DESCRIPTION

Chimeric Antigen Receptors (Cars)

Chimeric antigen receptors (CARs), also known as chimeric T cell receptors, artificial T cell receptors and chimeric immunoreceptors, are engineered receptors, which graft an arbitrary specificity onto an immune effector cell. In a classical CAR, the specificity of a monoclonal antibody is grafted on to a T cell. CAR-encoding nucleic acids may be transferred to T cells using, for example, retroviral vectors. In this way, a large number of cancer-specific T cells can be generated for adoptive cell transfer. Phase I clinical studies of this approach show efficacy.

The target-antigen binding domain of a CAR is commonly fused via a spacer and transmembrane domain to an endodomain. The endodomain may comprise or associate with an intracellular T-cell signalling domain. When the CAR binds the target-antigen, this results in the transmission of an activating signal to the T-cell it is expressed on.

The CAR of the present invention comprises a CD19 binding domain which is based on a mouse anti-CD19 monoclonal antibody.

The CAR of the present invention comprises a CD19-binding domain which comprises a) a heavy chain variable region (VH) having complementarity determining regions (CDRs) with the following sequences:

```
CDR1-
                            (SEQ ID No. 1)
GYAFSSS;

CDR2-
                            (SEQ ID No. 2)
YPGDED

CDR3-
                            (SEQ ID No. 3)
SLLYGDYLDY;
``` b) a light chain variable region (VL) having CDRs with the following sequences:

```
CDR1-
                            (SEQ ID No. 4)
SASSSVSYMH;

CDR2-
                            (SEQ ID No. 5)
DTSKLAS

CDR3-
                            (SEQ ID No. 6)
QQWNINPLT.
```

It may be possible to introduce one or more mutations (substitutions, additions or deletions) into each CDR without negatively affecting CD19-binding activity. Each CDR may, for example, have one, two or three amino acid mutations.

The CDRs may be in the format of a single-chain variable fragment (scFv), which is a fusion protein of the heavy variable region (VH) and light chain variable region (VL) of an antibody, connected with a short linker peptide of ten to about 25 amino acids. The scFv may be in the orientation VH-VL, i.e. the VH is at the amino-terminus of the CAR molecule and the VL domain is linked to the spacer and, in turn the transmembrane domain and endodomain.

The CDRs may be grafted on to the framework of a human antibody or scFv. For example, the CAR of the present invention may comprise a CD19-binding domain consisting or comprising one of the following sequences The CAR of the present invention may comprise the following VH sequence:

```
VH sequence from murine monoclonal antibody
                                         SEQ ID No. 7
QVQLQQSGPELVKPGASVKISCKASGYAFSSSWMNWVKQRPGKGLEWI
GRIYPGDEDTNYSGKFKDKATLTADKSSTTAYMQLSSLTSEDSAVYFC
ARSLLYGDYLDYWGQGTTLTVSS
```

The CAR of the present invention may comprise the following VL sequence:

```
VL sequence from murine monoclonal antibody
                                         SEQ ID No 8
QIVLTQSPAIMSASPGEKVTMTCSASSSVSYMHWYQQKSGTSPKRWIY
DTSKLASGVPDRFSGSGSGTSYFLTINNMEAEDAATYYCQQWNINPLT
FGAGTKLELKR
```

The CAR of the invention may comprise the following scFv sequence:

```
VH-VL scFv sequence from murine monoclonal
antibody
                                         SEQ ID No 9
QVQLQQSGPELVKPGASVKISCKASGYAFSSSWMNWVKQRPGKGLEWI
GRIYPGDEDTNYSGKFKDKATLTADKSSTTAYMQLSSLTSEDSAVYFC
ARSLLYGDYLDYWGQGTTLTVSSGGGGSGGGGSGGGGSQIVLTQSPAI
MSASPGEKVTMTCSASSSVSYMHWYQQKSGTSPKRWIYDTSKLASGVP
DRFSGSGSGTSYFLTINNMEAEDAATYYCQQWNINPLTFGAGTKLELK
R
```

The CAR may consist of or comprise one of the following sequences:

```
CAT19 CAR using "Campana" architecture
(see Examples)
                                         SEQ ID No. 10
MGTSLLCWMALCLLGADHADAQVQLQQSGPELVKPGASVKISCKASGY
AFSSSWMNWVKQRPGKGLEWIGRIYPGDEDTNYSGKFKDKATLTADKS
STTAYMQLSSLTSEDSAVYFCARSLLYGDYLDYWGQGTTLTVSSGGGG
SGGGGSGGGGSQIVLTQSPAIMSASPGEKVTMTCSASSSVSYMHWYQQ
KSGTSPKRWIYDTSKLASGVPDRFSGSGSGTSYFLTINNMEAEDAATY
YCQQWNINPLTFGAGTKLELKRSDPTTTPAPRPPTPAPTIASQPLSLR
PEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSA
DAPAYQQGQNQLYNELNLGRREEYDVLDKRRGRDPEMGGKPRRKNPQE
GLYNELQKDKMAEAYSEIGMKGERRRGKGHDGLYQGLSTATKDTYDAL
HMQALPPR CAT19 CAR with an OX40-Zeta endodomain
                                         SEQ ID No. 11
MGTSLLCWMALCLLGADHADAQVQLQQSGPELVKPGASVKISCKASGY
AFSSSWMNWVKQRPGKGLEWIGRIYPGDEDTNYSGKFKDKATLTADKS
STTAYMQLSSLTSEDSAVYFCARSLLYGDYLDYWGQGTTLTVSSGGGG
SGGGGSGGGGSQIVLTQSPAIMSASPGEKVTMTCSASSSVSYMHWYQQ
KSGTSPKRWIYDTSKLASGVPDRFSGSGSGTSYFLTINNMEAEDAATY
YCQQWNINPLTFGAGTKLELKRSDPTTTPAPRPPTPAPTIASQPLSLR
PEACRPAAGGAVHTRGLDFACDIYIWAPLAGTCGVLLLSLVITLYCRR
DQRLPPDAHKPPGGGSFRTPIQEEQADAHSTLAKIRVKFSRSADAPAY
QQGQNQLYNELNLGRREEYDVLDKRRGRDPEMGGKPRRKNPQEGLYNE
LQKDKMAEAYSEIGMKGERRRGKGHDGLYQGLSTATKDTYDALHMQAL
PPR CAT19 CAR with a CD28-Zeta endodomain
                                         SEQ ID No. 12
MGTSLLCWMALCLLGADHADAQVQLQQSGPELVKPGASVKISCKASGY
AFSSSWMNWVKQRPGKGLEWIGRIYPGDEDTNYSGKFKDKATLTADKS
STTAYMQLSSLTSEDSAVYFCARSLLYGDYLDYWGQGTTLTVSSGGGG
SGGGGSGGGGSQIVLTQSPAIMSASPGEKVTMTCSASSSVSYMHWYQQ
KSGTSPKRWIYDTSKLASGVPDRFSGSGSGTSYFLTINNMEAEDAATY
YCQQWNINPLTFGAGTKLELKRSDPTTTPAPRPPTPAPTIASQPLSLR
PEACRPAAGGAVHTRGLDFACDIYIWAPLAGTCGVLLLSLVITLYCRS
KRSRLLHSDYMNMTPRRPGPTRKHYQPYAPPRDFAAYRSRVKFSRSAD
APAYQQGQNQLYNELNLGRREEYDVLDKRRGRDPEMGGKPRRKNPQEG
LYNELQKDKMAEAYSEIGMKGERRRGKGHDGLYQGLSTATKDTYDALH
MQALPPR Third generation CD19 CAR
                                         SEQ ID No. 13
MGTSLLCWMALCLLGADHADAQVQLQQSGPELVKPGASVKISCKASGY
AFSSSWMNWVKQRPGKGLEWIGRIYPGDEDTNYSGKFKDKATLTADKS
STTAYMQLSSLTSEDSAVYFCARSLLYGDYLDYWGQGTTLTVSSGGGG
SGGGGSGGGGSQIVLTQSPAIMSASPGEKVTMTCSASSSVSYMHWYQQ
KSGTSPKRWIYDTSKLASGVPDRFSGSGSGTSYFLTINNMEAEDAATY
YCQQWNINPLTFGAGTKLELKRSDPTTTPAPRPPTPAPTIASQPLSLR
PEACRPAAGGAVHTRGLDFACDIFWVLVVVGGVLACYSLLVTVAFIIF
WVRSKRSRLLHSDYMNMTPRRPGPTRKHYQPYAPPRDFAAYRSRDQRL
```

-continued

PPDAHKPPGGGSFRTPIQEEQADAHSTLAKIRVKFSRSADAPAYQQGQ

NQLYNELNLGRREEYDVLDKRRGRDPEMGGKPRRKNPQEGLYNELQKD

KMAEAYSEIGMKGERRRGKGHDGLYQGLSTATKDTYDALHMQALPPR

CD19 CAR with IgG1 hinge spacer
SEQ ID No. 14
MGTSLLCWMALCLLGADHADAQVQLQQSGPELVKPGASVKISCKASGY

AFSSSWMNWVKQRPGKGLEWIGRIYPGDEDTNYSGKFKDKATLTADKS

STTAYMQLSSLTSEDSAVYFCARSLLYGDYLDYWGQGTTLTVSSGGGG

SGGGGSGGGGSQIVLTQSPAIMSASPGEKVTMTCSASSSVSYMHWYQQ

KSGTSPKRWIYDTSKLASGVPDRFSGSGSGTSYFLTINNMEAEDAATY

YCQQWNINPLTFGAGTKLELKRSDPAEPKSPDKTHTCPPCPKDPKFWV

LVVVGGVLACYSLLVTVAFIIFWVRSKRSRLLHSDYMNMTPRRPGPTR

KHYQPYAPPRDFAAYRSRVKFSRSADAPAYQQGQNQLYNELNLGRREE

YDVLDKRRGRDPEMGGKPRRKNPQEGLYNELQKDKMAEAYSEIGMKGE

RRRGKGHDGLYQGLSTATKDTYDALHMQALPPR

CD19 CAR with hinge-CH2-CH3 of human IgG1
with FcR binding sites mutated out
SEQ ID No. 15
MGTSLLCWMALCLLGADHADAQVQLQQSGPELVKPGASVKISCKASGY

AFSSSWMNWVKQRPGKGLEWIGRIYPGDEDTNYSGKFKDKATLTADKS

STTAYMQLSSLTSEDSAVYFCARSLLYGDYLDYWGQGTTLTVSSGGGG

SGGGGSGGGGSQIVLTQSPAIMSASPGEKVTMTCSASSSVSYMHWYQQ

KSGTSPKRWIYDTSKLASGVPDRFSGSGSGTSYFLTINNMEAEDAATY

YCQQWNINPLTFGAGTKLELKRSDPAEPKSPDKTHTCPPCPAPPVAGP

SVFLFPPKPKDTLMIARTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHE

ALHNHYTQKSLSLSPGKKDPKFWVLVVVGGVLACYSLLVTVAFIIFWV

RSKRSRLLHSDYMNMTPRRPGPTRKHYQPYAPPRDFAAYRSRVKFSRS

ADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDA

LHMQALPPR

The CAR of the invention may comprise a variant of the sequence shown as SEQ ID No. 7, 8, 9, 10, 11, 12, 13, 14 or 15 having at least 80, 85, 90, 95, 98 or 99% sequence identity, provided that the variant sequence retain the capacity to bind CD19 (when in conjunction with a complementary VL or VH domain, if appropriate).

The percentage identity between two polypeptide sequences may be readily determined by programs such as BLAST which is freely available at http://blast.ncbi.nlm.nih.gov.

Transmembrane Domain

The CAR of the invention may also comprise a transmembrane domain which spans the membrane. It may comprise a hydrophobic alpha helix. The transmembrane domain may be derived from CD28, which gives good receptor stability.

The transmembrane domain may comprise the sequence shown as SEQ ID No. 22.

SEQ ID No. 22
FWVLVVVGGVLACYSLLVTVAFIIFWV

Intracellular T Cell Signaling Domain (Endodomain)

The endodomain is the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, endodomains from CD28, or OX40 or 41BB can be used with CD3-Zeta to transmit a proliferative/survival signal, or all three can be used together.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains were constructed. Fusion of the intracellular part of a T-cell co-stimulatory molecule to that of CD3ζ resulted in second generation receptors which could transmit an activating and co-stimulatory signal simultaneously after antigen recognition. The co-stimulatory domain most commonly used was that of CD28. This supplies the most potent co-stimulatory signal, namely immunological signal 2, which triggers T-cell proliferation. Some receptors were also described which included TNF receptor family endodomains such as OX40 and 41BB which transmit survival signals. Finally, even more potent third generation CARs were described which had endodomains capable of transmitting activation, proliferation and survival signals. CARs and their different generations are summarized in FIG. 4.

The endodomain of the CAR of the present invention may comprise combinations of one or more of the CD3-Zeta endodomain, the 41BB endodomain, the OX40 endodomain or the CD28 endodomain.

The intracellular T-cell signalling domain (endodomain) of the CAR of the present invention may comprise the sequence shown as SEQ ID No. 23, 24, 25, 26, 27, 28, 29 or 30 or a variant thereof having at least 80% sequence identity.

(CD3 zeta endodomain)
SEQ ID No. 23
RSRVKFSRSADAPAYQQGQNQLYNELNLGRREEYDVLDKRRGRDPEMG

GKPRRKNPQEGLYNELQKDKMAEAYSEIGMKGERRRGKGHDGLYQGLS

TATKDTYDALHMQALPPR (41BB endodomain)
SEQ ID No. 24
KRGRKKLLYIFKQPFMRPVQTTQEEDGCSCRFPEEEEGGCEL (OX40 endodomain)
SEQ ID No. 25
RRDQRLPPDAHKPPGGGSFRTPIQEEQADAHSTLAKI (CD28 endodomain)
SEQ ID No. 26
KRSRLLHSDYMNMTPRRPGPTRKHYQPYAPPRDFAAY -continued Examples of combinations of such endodomains include 41BB-Z, OX40-Z, CD28-Z and CD28-OX40-Zeta.

(41BB-Z endodomain fusion)
SEQ ID No. 27
KRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNP

QEGLYNELQKDKMAEAYSEIGMKGERRRGKGHDGLYQGLSTATKDTYD

ALHMQALPPR (OX40-Z endodomain fusion)
SEQ ID No. 28
RRDQRLPPDAHKPPGGGSFRTPIQEEQADAHSTLAKIRVKFSRSADAP

AYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQ

ALPPR (CD28Z endodomain fusion)
SEQ ID No. 29
KRSRLLHSDYMNMTPRRPGPTRKHYQPYAPPRDFAAYRSRVKFSRSAD

APAYQQGQNQLYNELNLGRREEYDVLDKRRGRDPEMGGKPRRKNPQEG

LYNELQKDKMAEAYSEIGMKGERRRGKGHDGLYQGLSTATKDTYDALH

MQALPPR (CD28OXZ)
SEQ ID No. 30
KRSRLLHSDYMNMTPRRPGPTRKHYQPYAPPRDFAAYRSRDQRLPPDA

HKPPGGGSFRTPIQEEQADAHSTLAKIRVKFSRSADAPAYQQGQNQLY

NELNLGRREEYDVLDKRRGRDPEMGGKPRRKNPQEGLYNELQKDKMAE

AYSEIGMKGERRRGKGHDGLYQGLSTATKDTYDALHMQALPPR

A variant sequence may have at least 80%, 85%, 90%, 95%, 98% or 99% sequence identity to SEQ ID No. 22, 23, 24, 25, 26, 27, 28, 29 or 30 provided that the sequence provides an effective transmembrane domain/intracellular T cell signaling domain.

Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The CAR of the invention may have the general formula:

> Signal peptide—CD19-binding domain—spacer domain-transmembrane domain/intracellular T cell signaling domain.

The signal peptide may comprise the SEQ ID No. 31 or a variant thereof having 5, 4, 3, 2 or 1 amino acid mutations (insertions, substitutions or additions) provided that the signal peptide still functions to cause cell surface expression of the CAR.

SEQ ID No. 31:
METDTLLLWVLLLWVPGSTG

The signal peptide of SEQ ID No. 31 is compact and highly efficient. It is predicted to give about 95% cleavage after the terminal glycine, giving efficient removal by signal peptidase.

Spacer

The CAR of the present invention may comprise a spacer sequence to connect the CD19-binding domain with the transmembrane domain and spatially separate the CD19-binding domain from the endodomain. A flexible spacer allows to the CD19-binding domain to orient in different directions to enable CD19 binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

SEQ ID No. 32 (hinge-CH2CH3 of human IgG1)
AEPKSPDKTHTCPPCPAPPVAGPSVFLFPPKPKDTLMIARTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELT

KNQVSLTCLVKGFYPSDIAVEWESNGQPENNYKTTPPVLDSDGSFFLY

SKLTVDKSRWQQGNVFSCSVMHEALHNHYTQKSLSLSPGKKD

SEQ ID No. 33 (human CD8 stalk):
TTTPAPRPPTPAPTIASQPLSLRPEACRPAAGGAVHTRGLDFACDI

SEQ ID No. 34 (human IgG1 hinge):
AEPKSPDKTHTCPPCPKDPK

SEQ ID No. 35 (IgG1 Hinge-Fc)
AEPKSPDKTHTCPPCPAPELLGGPSVFLFPPKPKDTLMISRTPEVTCV

VVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFL

YSKLTVDKSRWQQGNVFSCSVMHEALHNHYTQKSLSLSPGKKDPK

SEQ ID No. 36 (IgG1 Hinge-Fc modified to remove
Fc receptor recognition motifs)
AEPKSPDKTHTCPPCPAPPVA*GPSVFLFPPKPKDTLMIARTPEVTCV

VVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFL

YSKLTVDKSRWQQGNVFSCSVMHEALHNHYTQKSLSLSPGKKDPK

Modified residues are underlined; * denotes a deletion.

Interferon Release and Car T-Cell Exhaustion

The present inventors have found that a CD19 CAR based on the CAT19 scFv has properties which may result in lower toxicity and better efficacy.

Given that the main experience with CD19 CAR therapy has been with CARs based on the fmc63 scFv, and that the oldest, largest and perhaps most significant clinical data set is with the fmc63 based Campana CAR, the present inventors took this Campana CAR as the "gold-standard". A comparison was hence made between the fmc63-Campana CAR and a similar CAR but with CAT19 scFv instead of fmc63. Surprisingly, the present inventors found that while CAT19 CAR T-cells effected killing of target cell expressing CD19, and proliferated in response to CD19 expressing targets, Interferon-gamma release was less. Further, a small animal model of an aggressive B-cell lymphoma showed equal efficacy and equal engraftment between the fmc63 and CAT19 based CARs, but surprisingly, less of the CAT19 CAR T-cells were exhausted than fmc63 CAR T-cells.

The CAR of the invention may cause 25, 50, 70 or 90% lower IFNγ release in a comparative assay involving bringing CAR T cells into contact with target cells.

The CAR of the invention may result in a smaller proportion of CAR T cells becoming exhausted than fmc63 CAR T cells. T cell exhaustion may be assessed using methods known in the art, such as analysis of PD-1 expression. The CAR of the present invention may cause 20, 30, 40, 50, 60 of 70% fewer CAR T cells to express PD-1 that fmc63 CAR T cells in a comparative assay involving bringing CAR T cells into contact with target cells.

Nucleic Acid Sequence

The second aspect of the invention relates to a nucleic acid sequence which codes for a CAR of the first aspect of the invention.

The nucleic acid sequence may be capable of encoding a CAR having the amino acid sequence shown as any of SEQ ID No. 10-15.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or a viral vector, such as a retroviral vector or a lentiviral vector.

The vector may be capable of transfecting or transducing a cell, such as a T cell.

Cell

The invention also provides a cell which comprises a nucleic acid according to the invention. The invention provides a cell which expresses a CAR according to the first aspect of the invention at the cell surface.

The cell may be a cytolytic immune cell, such as a T-cell or natural killer (NK) cell.

A cell capable of expressing a CAR according to the invention may be made by transducing or transfecting a cell with CAR-encoding nucleic acid.

The CAR-expressing cell of the invention may be generated ex vivo. The cell may be from a cell sample, such as a peripheral blood mononuclear cell (PBMC) sample from the patient or a donor. Cells may be activated and/or expanded prior to being transduced with CAR-encoding nucleic acid, for example by treatment with an anti-CD3 monoclonal antibody.

Pharmaceutical Composition

The present invention also relates to a pharmaceutical composition containing a CAR-expressing cell, or plurality of cells, of the invention together with a pharmaceutically acceptable carrier, diluent or excipient, and optionally one or more further pharmaceutically active polypeptides and/or compounds. Such a formulation may, for example, be in a form suitable for intravenous infusion.

Method of Treatment

CAR-expressing cells of the present invention may be capable of killing cancer cells, such as B-cell lymphoma cells. CAR-expressing cells, such as T-cells or NK cells, may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party). Alternatively, CAR-expressing cells may be derived from ex vivo differentiation of inducible progenitor cells or embryonic progenitor cells to cells such as T-cells. In these instances, CAR cells are generated by introducing DNA or RNA coding for the CAR by one of many means including transduction with a viral vector, transfection with DNA or RNA.

T or NK cells expressing a CAR molecule of the present invention may be used for the treatment of a cancerous disease, in particular a cancerous disease associated with CD19 expression.

A method for the treatment of disease relates to the therapeutic use of a cell or population of cells of the invention. In this respect, the cells may be administered to a subject having an existing disease or condition in order to lessen, reduce or improve at least one symptom associated with the disease and/or to slow down, reduce or block the progression of the disease. The method of the invention may cause or promote cell mediated killing of CD19-expressing cells, such as B cells.

The invention will now be further described by way of Examples, which are meant to serve to assist one of ordinary skill in the art in carrying out the invention and are not intended in any way to limit the scope of the invention.

EXAMPLES

Example 1—Cloning of VH and VL and Demonstration of CD19 Binding

The VH and VL were cloned from a mouse anti-CD19 monoclonal antibody and fused in frame with the human kappa constant region and the human IgG1 constant region. These chimeric heavy and light chains were cloned into an expression vector and used to transfect 293T cells. The subsequent produced antibody was used to stain SupT1 cells (a T-cell line which is CD19 negative), and SupT1 cells which have been engineered to be CD19 positive. This staining shows specific binding of the CD19 (FIG. 2).

Example 2—Demonstration that the VH/VL can Form an scFv which Binds CD19

It was then investigated whether the cloned VH and VL could bind CD19 in a scFv format. The VH and VL were cloned as an scFv in two orientations: VH-VL and VL-VH, where the two variable regions were separated by a linker comprising of (SGGGG)4. These scFv were cloned into a non-signalling CAR co-expressed with truncated CD34 as shown in FIG. 3a. Briefly, this comprises of a signal peptide, scFv, hinge-CH2-CH3 of human IgG1, the CD8 transmembrane domain, the first 12 residues of the CD8 endodomain, a FMD-2A peptide TeV, truncated human CD34. To allow comparison, scFv from fmc63, and scFv from another anti-CD19 hybridoma 4g7, were cloned in the same format in both VH-VL and VL-VH orientations.

In this way, several parameters can be studied: (1) the binding of target antigen to the CAR by use of recombinant cognate target antigen fused to murine Fc, unencumbered by internalization of the receptor due to signalling; (2) The stability of the receptor can be determined using polyclonal anti-Fc; (3) the expression levels of the cassette can be controlled for by co-staining for CD34.

These constructs were transduced into SupT1 cells. Recombinant CD19-mouse IgG2aFc fusion was generated. SupT1 cells were stained for mouse-Fc, human-Fc and anti-CD34 with antibodies conjugated to different fluorophores and stability/binding interrogated by flow-cytometery.

The sequences of the different scFvs used are detailed below:

```
>scFv_fmc63_VH-VL
                                          (SEQ ID No. 37)
EVKLQESGPGLVAPSQSLSVTCTVSGVSLPDYGVSWIRQPPRKGLEWL

GVIWGSETTYYNSALKSRLTIIKDNSKSQVFLKMNSLQTDDTAIYYCA

KHYYYGGSYAMDYWGQGTSVTVSSGGGGSGGGGSGGGGSDIQMTQTTS

SLSASLGDRVTISCRASQDISKYLNWYQQKPDGTVKLLIYHTSRLHSG

VPSRFSGSGSGTDYSLTISNLEQEDIATYFCQQGNTLPYTFGGGTKLE

ITKA

>scFv_fmc63_VL-VH
                                          (SEQ ID No. 38)
DIQMTQTTSSLSASLGDRVTISCRASQDISKYLNWYQQKPDGTVKLLI

YHTSRLHSGVPSRFSGSGSGTDYSLTISNLEQEDIATYFCQQGNTLPY

TFGGGTKLEITKAGGGGSGGGGSGGGGSEVKLQESGPGLVAPSQSLSV

TCTVSGVSLPDYGVSWIRQPPRKGLEWLGVIWGSETTYYNSALKSRLT

IIKDNSKSQVFLKMNSLQTDDTAIYYCAKHYYYGGSYAMDYWGQGTSV

TVSS

>scFv_4g7_VH-VL
                                          (SEQ ID No. 39)
EVQLQQSGPELIKPGASVKMSCKASGYTFTSYVMHWVKQKPGQGLEWI

GYINPYNDGTKYNEKFKGKATLTSDKSSSTAYMELSSLTSEDSAVYYC

ARGTYYYGSRVFDYWGQGTTLTVSSGGGGSGGGGSGGGGSDIVMTQAA

PSIPVTPGESVSISCRSSKSLLNSNGNTYLYWFLQRPGQSPQLLIYRM

SNLASGVPDRFSGSGSGTAFTLRISRVEAEDVGVYYCMQHLEYPFTFG

AGTKLELKR

>scFv_4g7_VL-VH
                                          (SEQ ID No. 40)
DIVMTQAAPSIPVTPGESVSISCRSSKSLLNSNGNTYLYWFLQRPGQS

PQLLIYRMSNLASGVPDRFSGSGSGTAFTLRISRVEAEDVGVYYCMQH

LEYPFTFGAGTKLELKRSGGGGSGGGGSGGGGSEVQLQQSGPELIKPG

ASVKMSCKASGYTFTSYVMHWVKQKPGQGLEWIGYINPYNDGTKYNEK

FKGKATLTSDKSSSTAYMELSSLTSEDSAVYYCARGTYYYGSRVFDYW

GQGTTLTVSS

>scFv_CAT_VH-VL
                                          (SEQ ID No. 9)
QVQLQQSGPELVKPGASVKISCKASGYAFSSSWMNWVKQRPGKGLEWI

GRIYPGDEDTNYSGKFKDKATLTADKSSTTAYMQLSSLTSEDSAVYFC

ARSLLYGDYLDYWGQGTTLTVSSGGGGSGGGGSGGGGSQIVLTQSPAI

MSASPGEKVTMTCSASSSVSYMHWYQQKSGTSPKRWIYDTSKLASGVP

DRFSGSGSGTSYFLTINNMEAEDAATYYCQQWNINPLTFGAGTKLELK

R

>scFv_CAT_VL-VH
                                          (SEQ ID No. 41)
QIVLTQSPAIMSASPGEKVTMTCSASSSVSYMHWYQQKSGTSPKRWIY

DTSKLASGVPDRFSGSGSGTSYFLTINNMEAEDAATYYCQQWNINPLT

FGAGTKLELKRSGGGGSGGGGSGGGGSQVQLQQSGPELVKPGASVKIS

CKASGYAFSSSWMNWVKQRPGKGLEWIGRIYPGDEDTNYSGKFKDKAT

LTADKSSTTAYMQLSSLTSEDSAVYFCARSLLYGDYLDYWGQGTTLTV

SS
```

The construct used and the staining results are summarized in FIG. 3. Surprisingly, the CAT CAR with scFv in VH-VL orientation binds CD19, while the CAT19 CAR with scFv in the VL-VH orientation gave minimal CD19 binding. This was in contrast to the fmc63 CARs and 4g7 CARs which bound CD19 in both the HL and LH orientations. Binding and stability of the HL CAT CAR appeared equal to that with fmc63.

Example 3—In Vitro Comparison of CAT19 CAR Function Against Fmc36 CAR

The CAT scFv in HL orientation was cloned into a CAR scaffold designed by Campana (Imai et al (2004) Leuk. Off. J. Leuk. Soc, Am. Leuk, Res. Fund. UK 18:676-684). Effectively the fmc63 scFv was replaced with a CAT scFv, and compared with the original fmc63 based CAR. This CAR comprises a signal peptide, the scFv, a CD8 stalk spacer and transmembrane and 41BB and Zeta endodomains. The amino acid sequences of the CAT CAR and fmc63 CAR are given below:

```
>CAT19_CAR
                                          (SEQ ID No. 10)
MGTSLLCWMALCLLGADHADAQVQLQQSGPELVKPGASVKISCKASGY

AFSSSWMNWVKQRPGKGLEWIGRIYPGDEDTNYSGKFKDKATLTADKS

STTAYMQLSSLTSEDSAVYFCARSLLYGDYLDYWGQGTTLTVSSGGGG

SGGGGSGGGGSQIVLTQSPAIMSASPGEKVTMTCSASSSVSYMHVVYQ

QKSGTSPKRWIYDTSKLASGVPDRFSGSGSGTSYFLTINNMEAEDAAT

YYCQQWNINPLTFGAGTKLELKRSDPTTTPAPRPPTPAPTIASQPLSL

RPEACRPAAGGAVHTRGLDFACDIYIWAPLAGTCGVLLLSLVITLYCK

RGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDA

LHMQALPPR
```

-continued

>Fmc63_CAR, as described by lmai et al (2004) as above (SEQ ID No. 42)
METDTLLLWVLLLWVPGSTGDIQMTQTTSSLSASLGDRVTISCRASQD

ISKYLNWYQQKPDGTVKLLIYHTSRLHSGVPSRFSGSGSGTDYSLTIS

NLEQEDIATYFCQQGNTLPYTFGGGTKLEITKAGGGGSGGGGSGGGGS

GGGGSEVKLQESGPGLVAPSQSLSVTCTVSGVSLPDYGVSWIRQPPRK

GLEWLGVIWGSETTYYNSALKSRLTIIKDNSKSQVFLKMNSLQTDDTA

IYYCAKHYYYGGSYAMDYWGQGTSVTVSSDPTTTPAPRPPTPAPTIAS

QPLSLRPEACRPAAGGAVHTRGLDFACDIYIWAPLAGTCGVLLLSLVI

TLYCKRGRKKLLYIFKQPFMRPVQTTQEEDGCSCRFPEEEEGGCELRV

KFSRSADAPAYQQGQNQLYNELNLGRREEYDVLDKRRGRDPEMGGKPR

RKNPQEGLYNELQKDKMAEAYSEIGMKGERRRGKGHDGLYQGLSTATK

DTYDALHMQALPPR

Primary human T-cells from 5 different donors were transduced with lentiviral vectors coding for CAT19 CAR in Campana format, or the fmc63 Campana CAR itself. These T-cells were then used in various assays. Chromium release assay was performed against SupT1 cells. These cells are CD19 negative. Neither CAR T-cells responded against this cell line demonstrating that CAR19 CAR has no non-specific killing activity against CD19 negative cells [FIG. 5(a)]. (b) Chromium release assay was also performed against SupT1 cells engineering to express CD19. Both CARs performed equally against this cell line in this assay with high-levels of killing [FIG. 5(b)]. Next a degranulation assay was performed by staining for CD107 on the surface of effector cells after co-culture with target cells. Here either NT T-cells, fmc63 CAR T-cells, or CAT19 CAR T-cells were used as effectors and either SupT1 or SupT1.CD19 cells were used as targets. Surface CD107 was detected by flow-cytometry which allowed differential measurement of degranulation of CD4+ and CD8+ cells. [FIGS. 5(c) and (d) respectively]. Degranulation was increased with CAT19 CAR T-cells in comparison with fmc63 CAR T-cells. Proliferation was estimated using tritiated thymidilate incorporation. Here, NT, fmc63 CAR T-cells, CAT19 CAR T-cells were co-cultured with SupT1 cells engineered to express CD19. Incorporation of thymidiln this experiment, an irrelevant CAR targeting GD2 was also tested. There was a trend to increased proliferation with CAR19 CAR T-cells [FIG. 4(e)]. Next, interferon-gamma release from either NT T-cells, fmc63 CAR T-cells, CAT19 CAR T-cells or GD2 CAR T-cells 24 hours after challenge against SupT1 or SupT1.CD19 cells was measured by ELISA. CAT19 CAR T-cells produced significantly less interferon-gamma than fmc63 CAR T-cells when challenged with CD19+ targets.

Example 4—Demonstration of In Vivo Efficacy of CAT19 CAR Therapy

An outline of experimental set-up for this in vivo model is present in FIG. 6(a). Briefly NSG (NOD scid gamma, NOD.Cg-Prkdc$^{scid}$ Il2rg$^{tm1Wjl}$/SzJ) mice are sufficiently immunocompromised that they are permissive for engraftment of human cell lines and primary human T-cells. Raji cells are a B-cell line derived from Burkitt's lymphoma. These cells readily engraft within the bone-marrow of NSG mice causing an aggressive leukaemia-like syndrome. Raji cells were engineered to express fire-fly Luciferase to allow non-invasive tracking using bioluminescence imaging (BLI). Mice were injected with $2.5 \times 10^{\wedge}5$ Raji.FLuc cells via tail vein injection. 24 hours later $4 \times 10^{\wedge}6$ of either NT primary human T-cells, or T-cells transduced with fmc63 CAR, or T-cells transduced with CAT19 CAR were administered via tail-vein. Tumour response was measured sequentially by BLI. Tail-vein blood was sampled at day 4 for engraftment and serum cytokine. The animals were culled at day 11 and tissues studied for persistence of CAR T-cells and tumour burden. BLI imaging of the different mouse cohorts at day 10 is shown in FIG. 6(b). Extensive disease is seen in the pelvis, spine, ribs, skull and spleen of mice treated with NT T-cells, while minimal signal is evident in mice who received either CAT19 CAR T-cells, or fmc63 CAR T-cells. Quantitative bioluminescent signal averaged from different mouse cohorts over time is shown on a log-scale in FIG. 6(c). A clear difference is seen between signal accumulation in mice who received NT T-cells, and mice who received CAR T-cells. No difference in signal accumulation is seen in mice who received fmc63 CAR T-cells or CAT19 CAR T-cells. Finally, after sacrifice, flow-cytometric analysis of bone-marrow from each mouse was performed to directly determine tumour burden. Raji cells are easily distinguishable from mouse haematopoietic cells and from adoptively transferred T-cells, since they express human B-cell markers. Minimal Raji cells could be detected in marrow of mice who received either fmc63 or CAT19 CAR T-cells.

Example 5—Characterization of In Vivo Persisting CAR T-Cells

From the above animal models, the present inventors sought to determine if both types of CAR T-cells engrafted within the bone-marrow and spleen of these NSG mice. Flow-cytometric analysis of bone-marrow and spleen with counting beads allowed determination of absolute numbers of CAR T-cells. This data is shown in FIGS. 7(a) and (b). The absolute numbers of CAR T-cells in spleens of mice from animals treated with fmc63 CAR T-cells or CAT19 CAR T-cells was similar. Next, the present inventors proceeded to determine if there was any difference in the numbers of exhausted T-cells in these different tissues. By co-staining for PD1 expression in the above samples the numbers of exhausted T-cells could be determined. This data is shown in FIGS. 7(c) and (d). Surprisingly, fewer exhausted T-cells were present in both tissue compartments with the CAT19 CAR than the fmc63 CAR.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, CAR technology or related fields are intended to be within the scope of the following claims.

The invention claimed is:

1. A method of causing cell-mediated killing of CD19-expressing cells in a subject, the method comprising a step of administering a composition to the subject, wherein the composition comprises a plurality of cells expressing a chimeric antigen receptor (CAR), said CAR comprising a CD19-binding domain which comprises:
   a) a heavy chain variable region (VH) having complementarity determining regions (CDRs) with the following sequences:

CDR1-
   GYAFSSS;    (SEQ ID NO: 1)

CDR2-
   YPGDED; and    (SEQ ID NO: 2)

CDR3-
   SLLYGDYLDY;    (SEQ ID NO: 3)

b) a light chain variable region (VL) having CDRs with the following sequences:

CDR1-
   SASSSVSYMH;    (SEQ ID NO: 4)

CDR2-
   DTSKLAS; and    (SEQ ID NO: 5)

CDR3-
   QQWNINPLT.    (SEQ ID NO: 6)

2. The method according to claim 1, wherein the CD19-binding domain comprises a VH domain having the sequence shown as SEQ ID NO: 7.

3. The method according to claim 2, wherein the CD19-binding domain comprises a VL domain having the sequence shown as SEQ ID NO: 8.

4. The method according to claim 1, wherein the CD19-binding domain comprises a VL domain having the sequence shown as SEQ ID NO: 8.

5. The method according to claim 1, wherein the CD19-binding domain comprises an scFv in the orientation VH-VL.

6. The method according to claim 5, wherein the CD19-binding domain comprises the sequence shown as SEQ ID NO: 9.

7. The method according to claim 1, wherein the CAR further comprises a transmembrane domain and an intracellular T-cell signalling domain.

8. The method according to claim 7, wherein the CAR further comprises a spacer connecting the CD19-binding domain to the transmembrane domain.

9. The method according to claim 8, wherein the spacer comprises one of the following: a human an IgG1 Fc domain; an IgG1 hinge; or a CD8 stalk.

10. The method according to claim 8, wherein the intracellular T-cell signalling domain comprises one or more of the following endodomains: a CD28 endodomain; a 41BB endodomain, an OX40 endodomain and a CD3-Zeta endodomain.

11. The method according to claim 10, wherein the intracellular T-cell signalling domain comprises the 41BB endodomain and the CD3-Zeta endodomain.

12. The method according to claim 10, wherein the intracellular T-cell signalling domain comprises the OX40 endodomain and the CD3-Zeta endodomain.

13. The method according to claim 10, wherein the intracellular T-cell signalling domain comprises the CD28 endodomain; the OX40 endodmain; and the CD3-Zeta endodomain.

14. The method according to claim 1, wherein the CAR comprises the sequence shown as any of SEQ ID NO: 10 to 15.

15. The method according to claim 1, wherein the CDRs are grafted on to a human or humanised framework.

16. The method according to claim 1, wherein the composition comprises a plurality of T cells that express the CAR.

17. The method according to claim 1, wherein the composition comprises a plurality of natural killer (NK) cells that express the CAR.

18. The method according to claim 1, wherein the composition further comprises a pharmaceutically acceptable carrier, diluent or excipient.

19. The method according to claim 1, further comprising steps of transducing or transfecting cells from the subject ex vivo with a vector containing a nucleic acid that encodes the CAR, then administering transfected cells back to the subject.

20. The method according to claim 1, wherein the subject has a cancerous disease associated with CD19 expression.

21. A chimeric antigen receptor (CAR) comprising a CD19-binding domain which comprises:

a) a heavy chain variable region (VH) having complementarity determining regions (CDRs) with the following sequences:

CDR1- GYAFSSS; (SEQ ID No. 1)

CDR2- YPGDED; and (SEQ ID No. 2)

CDR3- SLLYGDYLDY; (SEQ ID No. 3)

b) a light chain variable region (VL) having CDRs with the following sequences:

CDR1- SASSSVSYMH; (SEQ ID No. 4)

CDR2- DTSKLAS; and (SEQ ID No. 5)

CDR3- QQWNINPLT; (SEQ ID No. 6)

and
wherein the CAR further comprises a transmembrane domain and an intracellular T-cell signalling domain, wherein the intracellular T-cell signalling domain comprises a 41BB endodomain and a CD3-Zeta endodomain.

* * * * *

UNITED STATES PATENT AND TRADEMARK OFFICE
CERTIFICATE OF CORRECTION

PATENT NO. : 11,578,126 B2  
APPLICATION NO. : 16/573854  
DATED : February 14, 2023  
INVENTOR(S) : Martin Pulé et al.

Page 1 of 1

It is certified that error appears in the above-identified patent and that said Letters Patent is hereby corrected as shown below:

On the Title Page

Item (57), Line 5, "CDR1—GY-AFSSS" should be -- CDR1—GYAFSSS --.

In the Claims

At Column 68, Line 43, "endodmain;" should be -- endodomain; --.

Signed and Sealed this
Second Day of January, 2024

Katherine Kelly Vidal
*Director of the United States Patent and Trademark Office*

SEQUENCE LISTING

<160> NUMBER OF SEQ ID NOS: 43

<210> SEQ ID NO 1
<211> LENGTH: 7
<212> TYPE: PRT
<213> ORGANISM: Artificial Sequence
<220> FEATURE:
<223> OTHER INFORMATION: heavy chain variable region (VH)
      complementarity determining region (CDR) CDR1

<400> SEQUENCE: 1

Gly Tyr Ala Phe Ser Ser Ser
1               5

<210> SEQ ID NO 2
<211> LENGTH: 6
<212> TYPE: PRT
<213> ORGANISM: Artificial Sequence
<220> FEATURE:
<223> OTHER INFORMATION: VH CDR, CDR2

<400> SEQUENCE: 2

Tyr Pro Gly Asp Glu Asp
1               5

<210> SEQ ID NO 3
<211> LENGTH: 10
<212> TYPE: PRT
<213> ORGANISM: Artificial Sequence
<220> FEATURE:
<223> OTHER INFORMATION: VH CDR, CDR3

<400> SEQUENCE: 3

Ser Leu Leu Tyr Gly Asp Tyr Leu Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: light chain variable region (VL) CDR, CDR1

<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL CDR, CDR2

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL CDR, CDR3

<400> SEQUENCE: 6

Gln Gln Trp Asn Ile Asn Pro Leu Thr

<210> SEQ ID NO 7
<211> LENGTH: 119
<212> TYPE: PRT
<213> ORGANISM: Artificial Sequence
<220> FEATURE:
<223> OTHER INFORMATION: VH sequence from murine monoclonal antibody

<400> SEQUENCE: 7

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Glu Asp Thr Asn Tyr Ser Gly Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: VL sequence from murine monoclonal antibody

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Ser Tyr Phe Leu Thr Ile Asn Asn Met Glu Ala Glu
65                  70                  75                  80

Asp Ala Ala Thr Tyr Tyr Cys Gln Gln Trp Asn Ile Asn Pro Leu Thr
                85                  90                  95

Phe Gly Ala Gly Thr Lys Leu Glu Leu Lys Arg
            100                 105

<210> SEQ ID NO 9
<211> LENGTH: 241
<212> TYPE: PRT
<213> ORGANISM: Artificial Sequence
<220> FEATURE:
<223> OTHER INFORMATION: VH-VL scFv sequence from murine monoclonal
      antibody

<400> SEQUENCE: 9

Gln Val Gln Leu Gln Gln Ser Gly Pro Glu Leu Val Lys Pro Gly Ala

```
            1               5                   10                  15
        Ser Val Lys Ile Ser Cys Lys Ala Ser Gly Tyr Ala Phe Ser Ser Ser
                        20                  25                  30

Trp Met Asn Trp Val Lys Gln Arg Pro Gly Lys Gly Leu Glu Trp Ile
                    35                  40                  45

Gly Arg Ile Tyr Pro Gly Asp Glu Asp Thr Asn Tyr Ser Gly Lys Phe
            50                  55                  60

Lys Asp Lys Ala Thr Leu Thr Ala Asp Lys Ser Ser Thr Thr Ala Tyr
        65                  70                  75                  80

Met Gln Leu Ser Ser Leu Thr Ser Glu Asp Ser Ala Val Tyr Phe Cys
                        85                  90                  95

Ala Arg Ser Leu Leu Tyr Gly Asp Tyr Leu Asp Tyr Trp Gly Gln Gly
                    100                 105                 110

Thr Thr Leu Thr Val Ser Ser Gly Gly Gly Ser Gly Gly Gly
                    115                 120                 125

Ser Gly Gly Gly Gly Ser Gln Ile Val Leu Thr Gln Ser Pro Ala Ile
            130                 135                 140

Met Ser Ala Ser Pro Gly Glu Lys Val Thr Met Thr Cys Ser Ala Ser
        145                 150                 155                 160

Ser Ser Val Ser Tyr Met His Trp Tyr Gln Gln Lys Ser Gly Thr Ser
                        165                 170                 175

Pro Lys Arg Trp Ile Tyr Asp Thr Ser Lys Leu Ala Ser Gly Val Pro
                    180                 185                 190

Asp Arg Phe Ser Gly Ser Gly Ser Gly Thr Ser Tyr Phe Leu Thr Ile
                195                 200                 205

Asn Asn Met Glu Ala Glu Asp Ala Ala Thr Tyr Tyr Cys Gln Gln Trp
                210                 215                 220

Asn Ile Asn Pro Leu Thr Phe Gly Ala Gly Thr Lys Leu Glu Leu Lys
        225                 230                 235                 240

Arg

<210> SEQ ID NO 10
<211> LENGTH: 488
<212> TYPE: PRT
<213> ORGANISM: Artificial Sequence
<220> FEATURE:
<223> OTHER INFORMATION: CAT19 chimeric antigen receptor (CAR) using
      "Campana" architecture

<400> SEQUENCE: 10

Met Gly Thr Ser Leu Leu Cys Trp Met Ala Leu Cys Leu Leu Gly Ala
        1               5                   10                  15

Asp His Ala Asp Ala Gln Val Gln Leu Gln Gln Ser Gly Pro Glu Leu
                        20                  25                  30

Val Lys Pro Gly Ala Ser Val Lys Ile Ser Cys Lys Ala Ser Gly Tyr
                    35                  40                  45

Ala Phe Ser Ser Ser Trp Met Asn Trp Val Lys Gln Arg Pro Gly Lys
            50                  55                  60

Gly Leu Glu Trp Ile Gly Arg Ile Tyr Pro Gly Asp Glu Asp Thr Asn
        65                  70                  75                  80

Tyr Ser Gly Lys Phe Lys Asp Lys Ala Thr Leu Thr Ala Asp Lys Ser
                        85                  90                  95

Ser Thr Thr Ala Tyr Met Gln Leu Ser Ser Leu Thr Ser Glu Asp Ser
                    100                 105                 110

Ala Val Tyr Phe Cys Ala Arg Ser Leu Leu Tyr Gly Asp Tyr Leu Asp
```

```
            115                 120                 125
Tyr Trp Gly Gln Gly Thr Thr Leu Thr Val Ser Ser Gly Gly Gly
        130                 135                 140
Ser Gly Gly Gly Gly Ser Gly Gly Gly Gly Ser Gln Ile Val Leu Thr
145                 150                 155                 160
Gln Ser Pro Ala Ile Met Ser Ala Ser Pro Gly Glu Lys Val Thr Met
                165                 170                 175
Thr Cys Ser Ala Ser Ser Val Ser Tyr Met His Trp Tyr Gln Gln
            180                 185                 190
Lys Ser Gly Thr Ser Pro Lys Arg Trp Ile Tyr Asp Thr Ser Lys Leu
            195                 200                 205
Ala Ser Gly Val Pro Asp Arg Phe Ser Gly Ser Gly Ser Gly Thr Ser
210                 215                 220
Tyr Phe Leu Thr Ile Asn Asn Met Glu Ala Glu Asp Ala Ala Thr Tyr
225                 230                 235                 240
Tyr Cys Gln Gln Trp Asn Ile Asn Pro Leu Thr Phe Gly Ala Gly Thr
                245                 250                 255
Lys Leu Glu Leu Lys Arg Ser Asp Pro Thr Thr Thr Pro Ala Pro Arg
            260                 265                 270
Pro Pro Thr Pro Ala Pro Thr Ile Ala Ser Gln Pro Leu Ser Leu Arg
                275                 280                 285
Pro Glu Ala Cys Arg Pro Ala Ala Gly Gly Ala Val His Thr Arg Gly
            290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
            355                 360                 365
Glu Glu Glu Gly Gly Cys Glu Leu Arg Val Lys Phe Ser Arg Ser Ala
        370                 375                 380
Asp Ala Pro Ala Tyr Gln Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
            435                 440                 445
Glu Ile Gly Met Lys Gly Glu Arg Arg Arg Gly Lys Gly His Asp Gly
        450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485

<210> SEQ ID NO 11
<211> LENGTH: 483
<212> TYPE: PRT
<213> ORGANISM: Artificial Sequence
<220> FEATURE:
<223> OTHER INFORMATION: CAT19 CAR with an OX40-Zeta endodomain
```

<400> SEQUENCE: 11

```
Met Gly Thr Ser Leu Leu Cys Trp Met Ala Leu Cys Leu Leu Gly Ala
1               5                   10                  15

Asp His Ala Asp Ala Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Trp Met Asn Trp Val Lys Gln Arg Pro Gly Lys
    50                  55                  60

Gly Leu Glu Trp Ile Gly Arg Ile Tyr Pro Gly Asp Glu Asp Thr Asn
65                  70                  75                  80

Tyr Ser Gly Lys Phe Lys Asp Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Phe Cys Ala Arg Ser Leu Leu Tyr Gly Asp Tyr Leu Asp
        115                 120                 125

Tyr Trp Gly Gln Gly Thr Thr Leu Thr Val Ser Ser Gly Gly Gly Gly
    130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Asp Arg Phe Ser Gly Ser Gly Ser Gly Thr Ser
    210                 215                 220

Tyr Phe Leu Thr Ile Asn Asn Met Glu Ala Glu Asp Ala Ala Thr Tyr
225                 230                 235                 240

Tyr Cys Gln Gln Trp Asn Ile Asn Pro Leu Thr Phe Gly Ala Gly Thr
                245                 250                 255

Lys Leu Glu Leu Lys Arg Ser Asp Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Arg
                325                 330                 335

Asp Gln Arg Leu Pro Pro Asp Ala His Lys Pro Pro Gly Gly Gly Ser
            340                 345                 350

Phe Arg Thr Pro Ile Gln Glu Glu Gln Ala Asp Ala His Ser Thr Leu
        355                 360                 365

Ala Lys Ile Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415
```

-continued

```
Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
            450                 455                 460

Ser Thr Ala Thr Lys Asp Thr Tyr Asp Ala Leu His Met Gln Ala Leu
465                 470                 475                 480

Pro Pro Arg

<210> SEQ ID NO 12
<211> LENGTH: 487
<212> TYPE: PRT
<213> ORGANISM: Artificial Sequence
<220> FEATURE:
<223> OTHER INFORMATION: CAT19 CAR with a CD28-Zeta endodomain

<400> SEQUENCE: 12

Met Gly Thr Ser Leu Leu Cys Trp Met Ala Leu Cys Leu Leu Gly Ala
1               5                   10                  15

Asp His Ala Asp Ala Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Lys
    50                  55                  60

Gly Leu Glu Trp Ile Gly Arg Ile Tyr Pro Gly Asp Glu Asp Thr Asn
65                  70                  75                  80

Tyr Ser Gly Lys Phe Lys Asp Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Phe Cys Ala Arg Ser Leu Leu Tyr Gly Asp Tyr Leu Asp
        115                 120                 125

Tyr Trp Gly Gln Gly Thr Thr Leu Thr Val Ser Ser Gly Gly Gly Gly
    130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Asp Arg Phe Ser Gly Ser Gly Ser Gly Thr Ser
    210                 215                 220

Tyr Phe Leu Thr Ile Asn Asn Met Glu Ala Glu Asp Ala Ala Thr Tyr
225                 230                 235                 240

Tyr Cys Gln Gln Trp Asn Ile Asn Pro Leu Thr Phe Gly Ala Gly Thr
                245                 250                 255

Lys Leu Glu Leu Lys Arg Ser Asp Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285
```

-continued

```
Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 13
<211> LENGTH: 527
<212> TYPE: PRT
<213> ORGANISM: Artificial Sequence
<220> FEATURE:
<223> OTHER INFORMATION: Third generation CD19 CAR

<400> SEQUENCE: 13

Met Gly Thr Ser Leu Leu Cys Trp Met Ala Leu Cys Leu Leu Gly Ala
1               5                   10                  15

Asp His Ala Asp Ala Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Lys
    50                  55                  60

Gly Leu Glu Trp Ile Gly Arg Ile Tyr Pro Gly Asp Glu Asp Thr Asn
65                  70                  75                  80

Tyr Ser Gly Lys Phe Lys Asp Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Phe Cys Ala Arg Ser Leu Leu Tyr Gly Asp Tyr Leu Asp
        115                 120                 125

Tyr Trp Gly Gln Gly Thr Thr Leu Thr Val Ser Ser Gly Gly Gly Gly
    130                 135                 140

Ser Gly Gly Gly Gly Ser Gly Gly Gly Gly Ser Gln Ile Val Leu Thr
145                 150                 155                 160
```

```
Gln Ser Pro Ala Ile Met Ser Ala Ser Pro Gly Glu Lys Val Thr Met
                165                 170                 175

Thr Cys Ser Ala Ser Ser Val Ser Tyr Met His Trp Tyr Gln Gln
        180                 185                 190

Lys Ser Gly Thr Ser Pro Lys Arg Trp Ile Tyr Asp Thr Ser Lys Leu
            195                 200                 205

Ala Ser Gly Val Pro Asp Arg Phe Ser Gly Ser Gly Ser Gly Thr Ser
210                 215                 220

Tyr Phe Leu Thr Ile Asn Asn Met Glu Ala Glu Asp Ala Ala Thr Tyr
225                 230                 235                 240

Tyr Cys Gln Gln Trp Asn Ile Asn Pro Leu Thr Phe Gly Ala Gly Thr
                245                 250                 255

Lys Leu Glu Leu Lys Arg Ser Asp Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
290                 295                 300

Leu Asp Phe Ala Cys Asp Ile Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
                340                 345                 350

Met Thr Pro Arg Arg Pro Gly Pro Thr Arg Lys His Tyr Gln Pro Tyr
            355                 360                 365

Ala Pro Pro Arg Asp Phe Ala Ala Tyr Arg Ser Arg Asp Gln Arg Leu
370                 375                 380

Pro Pro Asp Ala His Lys Pro Pro Gly Gly Gly Ser Phe Arg Thr Pro
385                 390                 395                 400

Ile Gln Glu Glu Gln Ala Asp Ala His Ser Thr Leu Ala Lys Ile Arg
                405                 410                 415

Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
        435                 440                 445

Val Leu Asp Lys Arg Arg Gly Arg Asp Pro Glu Met Gly Gly Lys Pro
    450                 455                 460

Arg Arg Lys Asn Pro Gln Glu Gly Leu Tyr Asn Glu Leu Gln Lys Asp
465                 470                 475                 480

Lys Met Ala Glu Ala Tyr Ser Glu Ile Gly Met Lys Gly Glu Arg Arg
                485                 490                 495

Arg Gly Lys Gly His Asp Gly Leu Tyr Gln Gly Leu Ser Thr Ala Thr
            500                 505                 510

Lys Asp Thr Tyr Asp Ala Leu His Met Gln Ala Leu Pro Pro Arg
        515                 520                 525

<210> SEQ ID NO 14
<211> LENGTH: 465
<212> TYPE: PRT
<213> ORGANISM: Artificial Sequence
<220> FEATURE:
<223> OTHER INFORMATION: CD19 CAR with IgG1 hinge spacer

<400> SEQUENCE: 14
```

```
Met Gly Thr Ser Leu Leu Cys Trp Met Ala Leu Cys Leu Leu Gly Ala
1               5                   10                  15

Asp His Ala Asp Ala Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
            35                  40                  45

Ala Phe Ser Ser Ser Trp Met Asn Trp Val Lys Gln Arg Pro Gly Lys
        50                  55                  60

Gly Leu Glu Trp Ile Gly Arg Ile Tyr Pro Gly Asp Glu Asp Thr Asn
65                  70                  75                  80

Tyr Ser Gly Lys Phe Lys Asp Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Phe Cys Ala Arg Ser Leu Leu Tyr Gly Asp Tyr Leu Asp
            115                 120                 125

Tyr Trp Gly Gln Gly Thr Thr Leu Thr Val Ser Ser Gly Gly Gly Gly
        130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
            180                 185                 190

Lys Ser Gly Thr Ser Pro Lys Arg Trp Ile Tyr Asp Thr Ser Lys Leu
            195                 200                 205

Ala Ser Gly Val Pro Asp Arg Phe Ser Gly Ser Gly Ser Gly Thr Ser
            210                 215                 220

Tyr Phe Leu Thr Ile Asn Asn Met Glu Ala Glu Asp Ala Ala Thr Tyr
225                 230                 235                 240

Tyr Cys Gln Gln Trp Asn Ile Asn Pro Leu Thr Phe Gly Ala Gly Thr
                245                 250                 255

Lys Leu Glu Leu Lys Arg Ser Asp Pro Ala Glu Pro Lys Ser Pro Asp
            260                 265                 270

Lys Thr His Thr Cys Pro Pro Cys Pro Lys Asp Pro Lys Phe Trp Val
            275                 280                 285

Leu Val Val Val Gly Gly Val Leu Ala Cys Tyr Ser Leu Leu Val Thr
290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
            325                 330                 335

Lys His Tyr Gln Pro Tyr Ala Pro Pro Arg Asp Phe Ala Ala Tyr Arg
            340                 345                 350

Ser Arg Val Lys Phe Ser Arg Ser Ala Asp Ala Pro Ala Tyr Gln Gln
            355                 360                 365

Gly Gln Asn Gln Leu Tyr Asn Glu Leu Asn Leu Gly Arg Arg Glu Glu
        370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
            405                 410                 415

Lys Asp Lys Met Ala Glu Ala Tyr Ser Glu Ile Gly Met Lys Gly Glu
```

```
            420                 425                 430
Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465

<210> SEQ ID NO 15
<211> LENGTH: 681
<212> TYPE: PRT
<213> ORGANISM: Artificial Sequence
<220> FEATURE:
<223> OTHER INFORMATION: CD19 CAR with hinge-CH2-CH3 of human IgG1, FcR
      binding sites mutated out

<400> SEQUENCE: 15

Met Gly Thr Ser Leu Leu Cys Trp Met Ala Leu Cys Leu Leu Gly Ala
1               5                   10                  15

Asp His Ala Asp Ala Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Lys
    50                  55                  60

Gly Leu Glu Trp Ile Gly Arg Ile Tyr Pro Gly Asp Glu Asp Thr Asn
65                  70                  75                  80

Tyr Ser Gly Lys Phe Lys Asp Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Phe Cys Ala Arg Ser Leu Leu Tyr Gly Asp Tyr Leu Asp
        115                 120                 125

Tyr Trp Gly Gln Gly Thr Thr Leu Thr Val Ser Ser Gly Gly Gly Gly
    130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Asp Arg Phe Ser Gly Ser Gly Ser Gly Thr Ser
    210                 215                 220

Tyr Phe Leu Thr Ile Asn Asn Met Glu Ala Glu Asp Ala Ala Thr Tyr
225                 230                 235                 240

Tyr Cys Gln Gln Trp Asn Ile Asn Pro Leu Thr Phe Gly Ala Gly Thr
                245                 250                 255

Lys Leu Glu Leu Lys Arg Ser Asp Pro Ala Glu Pro Lys Ser Pro Asp
            260                 265                 270

Lys Thr His Thr Cys Pro Pro Cys Pro Ala Pro Val Ala Gly Pro
        275                 280                 285

Ser Val Phe Leu Phe Pro Pro Lys Pro Lys Asp Thr Leu Met Ile Ala
    290                 295                 300
```

```
Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
            325                 330                 335

Ala Lys Thr Lys Pro Arg Glu Glu Gln Tyr Asn Ser Thr Tyr Arg Val
        340                 345                 350

Val Ser Val Leu Thr Val Leu His Gln Asp Trp Leu Asn Gly Lys Glu
    355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
            405                 410                 415

Cys Leu Val Lys Gly Phe Tyr Pro Ser Asp Ile Ala Val Glu Trp Glu
        420                 425                 430

Ser Asn Gly Gln Pro Glu Asn Asn Tyr Lys Thr Thr Pro Pro Val Leu
    435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
            485                 490                 495

Lys Lys Asp Pro Lys Phe Trp Val Leu Val Val Val Gly Gly Val Leu
        500                 505                 510

Ala Cys Tyr Ser Leu Leu Val Thr Val Ala Phe Ile Ile Phe Trp Val
    515                 520                 525

Arg Ser Lys Arg Ser Arg Leu Leu His Ser Asp Tyr Met Asn Met Thr
530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Arg Val Lys Phe Ser Arg Ser
            565                 570                 575

Ala Asp Ala Pro Ala Tyr Gln Gln Gly Gln Asn Gln Leu Tyr Asn Glu
        580                 585                 590

Leu Asn Leu Gly Arg Arg Glu Glu Tyr Asp Val Leu Asp Lys Arg Arg
    595                 600                 605

Gly Arg Asp Pro Glu Met Gly Gly Lys Pro Arg Arg Lys Asn Pro Gln
610                 615                 620

Glu Gly Leu Tyr Asn Glu Leu Gln Lys Asp Lys Met Ala Glu Ala Tyr
625                 630                 635                 640

Ser Glu Ile Gly Met Lys Gly Glu Arg Arg Arg Gly Lys Gly His Asp
            645                 650                 655

Gly Leu Tyr Gln Gly Leu Ser Thr Ala Thr Lys Asp Thr Tyr Asp Ala
        660                 665                 670

Leu His Met Gln Ala Leu Pro Pro Arg
    675                 680

<210> SEQ ID NO 16
<211> LENGTH: 7
<212> TYPE: PRT
<213> ORGANISM: Artificial Sequence
<220> FEATURE:
<223> OTHER INFORMATION: VH CDR, CDR1
```

<400> SEQUENCE: 16

Gly Val Ser Leu Pro Asp Tyr
1               5

<210> SEQ ID NO 17
<211> LENGTH: 5
<212> TYPE: PRT
<213> ORGANISM: Artificial Sequence
<220> FEATURE:
<223> OTHER INFORMATION: VH CDR, CDR2

<400> SEQUENCE: 17

Trp Gly Ser Glu Thr
1               5

<210> SEQ ID NO 18
<211> LENGTH: 12
<212> TYPE: PRT
<213> ORGANISM: Artificial Sequence
<220> FEATURE:
<223> OTHER INFORMATION: VH CDR, CDR3

<400> SEQUENCE: 18

His Tyr Tyr Tyr Gly Gly Ser Tyr Ala Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: VL CDR, CDR1

<400> SEQUENCE: 19

Arg Ala Ser Gln Asp Ile Ser Lys Tyr Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: VL CDR, CDR2

<400> SEQUENCE: 20

His Thr Ser Arg Leu His Ser
1               5

<210> SEQ ID NO 21
<211> LENGTH: 9
<212> TYPE: PRT
<213> ORGANISM: Artificial Sequence
<220> FEATURE:
<223> OTHER INFORMATION: VL CDR, CDR3

<400> SEQUENCE: 21

Gln Gln Gly Asn Thr Leu Pro Tyr Thr
1               5

<210> SEQ ID NO 22
<211> LENGTH: 27
<212> TYPE: PRT
<213> ORGANISM: Artificial Sequence
<220> FEATURE:
<223> OTHER INFORMATION: transmembrane domain

```
<400> SEQUENCE: 22

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 23
<211> LENGTH: 114
<212> TYPE: PRT
<213> ORGANISM: Artificial Sequence
<220> FEATURE:
<223> OTHER INFORMATION: CD3 zeta endodomain

<400> SEQUENCE: 23

Arg Ser Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
            20                  25                  30

Glu Tyr Asp Val Leu Asp Lys Arg Arg Gly Arg Asp Pro Glu Met Gly
        35                  40                  45

Gly Lys Pro Arg Arg Lys Asn Pro Gln Glu Gly Leu Tyr Asn Glu Leu
50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 24
<211> LENGTH: 42
<212> TYPE: PRT
<213> ORGANISM: Artificial Sequence
<220> FEATURE:
<223> OTHER INFORMATION: 41BB endodomain

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 25
<211> LENGTH: 37
<212> TYPE: PRT
<213> ORGANISM: Artificial Sequence
<220> FEATURE:
<223> OTHER INFORMATION: OX40 endodomain

<400> SEQUENCE: 25

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
            35
```

```
<210> SEQ ID NO 26
<211> LENGTH: 37
<212> TYPE: PRT
<213> ORGANISM: Artificial Sequence
<220> FEATURE:
<223> OTHER INFORMATION: CD28 endodomain

<400> SEQUENCE: 26

Lys Arg Ser Arg Leu Leu His Ser Asp Tyr Met Asn Met Thr Pro Arg
1               5                   10                  15

Arg Pro Gly Pro Thr Arg Lys His Tyr Gln Pro Tyr Ala Pro Pro Arg
                20                  25                  30

Asp Phe Ala Ala Tyr
            35

<210> SEQ ID NO 27
<211> LENGTH: 154
<212> TYPE: PRT
<213> ORGANISM: Artificial Sequence
<220> FEATURE:
<223> OTHER INFORMATION: 41BB-Z endodomain fusion

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu Arg Val Lys Phe Ser Arg
            35                  40                  45

Ser Ala Asp Ala Pro Ala Tyr Gln Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150

<210> SEQ ID NO 28
<211> LENGTH: 149
<212> TYPE: PRT
<213> ORGANISM: Artificial Sequence
<220> FEATURE:
<223> OTHER INFORMATION: OX40-Z endodomain fusion

<400> SEQUENCE: 28

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
                20                  25                  30

Thr Leu Ala Lys Ile Arg Val Lys Phe Ser Arg Ser Ala Asp Ala Pro
            35                  40                  45

Ala Tyr Gln Gln Gly Gln Asn Gln Leu Tyr Asn Glu Leu Asn Leu Gly
```

```
                    50                  55                  60
Arg Arg Glu Glu Tyr Asp Val Leu Asp Lys Arg Arg Gly Arg Asp Pro
 65                  70                  75                  80

Glu Met Gly Gly Lys Pro Arg Arg Lys Asn Pro Gln Glu Gly Leu Tyr
                 85                  90                  95

Asn Glu Leu Gln Lys Asp Lys Met Ala Glu Ala Tyr Ser Glu Ile Gly
            100                 105                 110

Met Lys Gly Glu Arg Arg Arg Gly Lys Gly His Asp Gly Leu Tyr Gln
            115                 120                 125

Gly Leu Ser Thr Ala Thr Lys Asp Thr Tyr Asp Ala Leu His Met Gln
            130                 135                 140

Ala Leu Pro Pro Arg
145

<210> SEQ ID NO 29
<211> LENGTH: 151
<212> TYPE: PRT
<213> ORGANISM: Artificial Sequence
<220> FEATURE:
<223> OTHER INFORMATION: CD28Z endodomain fusion

<400> SEQUENCE: 29

Lys Arg Ser Arg Leu Leu His Ser Asp Tyr Met Asn Met Thr Pro Arg
 1               5                  10                  15

Arg Pro Gly Pro Thr Arg Lys His Tyr Gln Pro Tyr Ala Pro Pro Arg
                20                  25                  30

Asp Phe Ala Ala Tyr Arg Ser Arg Val Lys Phe Ser Arg Ser Ala Asp
            35                  40                  45

Ala Pro Ala Tyr Gln Gln Gly Gln Asn Gln Leu Tyr Asn Glu Leu Asn
 50                  55                  60

Leu Gly Arg Arg Glu Glu Tyr Asp Val Leu Asp Lys Arg Arg Gly Arg
 65                  70                  75                  80

Asp Pro Glu Met Gly Gly Lys Pro Arg Arg Lys Asn Pro Gln Glu Gly
                85                  90                  95

Leu Tyr Asn Glu Leu Gln Lys Asp Lys Met Ala Glu Ala Tyr Ser Glu
            100                 105                 110

Ile Gly Met Lys Gly Glu Arg Arg Arg Gly Lys Gly His Asp Gly Leu
            115                 120                 125

Tyr Gln Gly Leu Ser Thr Ala Thr Lys Asp Thr Tyr Asp Ala Leu His
            130                 135                 140

Met Gln Ala Leu Pro Pro Arg
145                 150

<210> SEQ ID NO 30
<211> LENGTH: 187
<212> TYPE: PRT
<213> ORGANISM: Artificial Sequence
<220> FEATURE:
<223> OTHER INFORMATION: CD28OXZ

<400> SEQUENCE: 30

Lys Arg Ser Arg Leu Leu His Ser Asp Tyr Met Asn Met Thr Pro Arg
 1               5                  10                  15

Arg Pro Gly Pro Thr Arg Lys His Tyr Gln Pro Tyr Ala Pro Pro Arg
                20                  25                  30

Asp Phe Ala Ala Tyr Arg Ser Arg Asp Gln Arg Leu Pro Pro Asp Ala
            35                  40                  45
```

```
His Lys Pro Gly Gly Gly Ser Phe Arg Thr Pro Ile Gln Glu Glu
    50              55                  60

Gln Ala Asp Ala His Ser Thr Leu Ala Lys Ile Arg Val Lys Phe Ser
 65              70                  75                  80

Arg Ser Ala Asp Ala Pro Ala Tyr Gln Gln Gly Gln Asn Gln Leu Tyr
                 85                  90                  95

Asn Glu Leu Asn Leu Gly Arg Arg Glu Glu Tyr Asp Val Leu Asp Lys
            100                 105                 110

Arg Arg Gly Arg Asp Pro Glu Met Gly Gly Lys Pro Arg Arg Lys Asn
            115                 120                 125

Pro Gln Glu Gly Leu Tyr Asn Glu Leu Gln Lys Asp Lys Met Ala Glu
        130                 135                 140

Ala Tyr Ser Glu Ile Gly Met Lys Gly Glu Arg Arg Arg Gly Lys Gly
145                 150                 155                 160

His Asp Gly Leu Tyr Gln Gly Leu Ser Thr Ala Thr Lys Asp Thr Tyr
                165                 170                 175

Asp Ala Leu His Met Gln Ala Leu Pro Pro Arg
            180                 185

<210> SEQ ID NO 31
<211> LENGTH: 20
<212> TYPE: PRT
<213> ORGANISM: Artificial Sequence
<220> FEATURE:
<223> OTHER INFORMATION: signal peptide

<400> SEQUENCE: 31

Met Glu Thr Asp Thr Leu Leu Leu Trp Val Leu Leu Leu Trp Val Pro
1               5                   10                  15

Gly Ser Thr Gly
            20

<210> SEQ ID NO 32
<211> LENGTH: 234
<212> TYPE: PRT
<213> ORGANISM: Artificial Sequence
<220> FEATURE:
<223> OTHER INFORMATION: spacer (hinge-CH2CH3 of human IgG1)

<400> SEQUENCE: 32

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
 65                 70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 33
<211> LENGTH: 46
<212> TYPE: PRT
<213> ORGANISM: Artificial Sequence
<220> FEATURE:
<223> OTHER INFORMATION: spacer (human CD8 stalk)

<400> SEQUENCE: 33

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 34
<211> LENGTH: 20
<212> TYPE: PRT
<213> ORGANISM: Artificial Sequence
<220> FEATURE:
<223> OTHER INFORMATION: spacer (human IgG1 hinge)

<400> SEQUENCE: 34

Ala Glu Pro Lys Ser Pro Asp Lys Thr His Thr Cys Pro Pro Cys Pro
1               5                   10                  15

Lys Asp Pro Lys
            20

<210> SEQ ID NO 35
<211> LENGTH: 237
<212> TYPE: PRT
<213> ORGANISM: Artificial Sequence
<220> FEATURE:
<223> OTHER INFORMATION: spacer (IgG1 Hinge-Fc)

<400> SEQUENCE: 35

Ala Glu Pro Lys Ser Pro Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

```
Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235

<210> SEQ ID NO 36
<211> LENGTH: 236
<212> TYPE: PRT
<213> ORGANISM: Artificial Sequence
<220> FEATURE:
<223> OTHER INFORMATION: spacer (IgG1 Hinge - Fc modified to remove Fc
      receptor recognition motifs)

<400> SEQUENCE: 36

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
    210                 215                 220

Ser Leu Ser Leu Ser Pro Gly Lys Lys Asp Pro Lys
225                 230                 235

<210> SEQ ID NO 37
<211> LENGTH: 244
<212> TYPE: PRT
<213> ORGANISM: Artificial Sequence
<220> FEATURE:
<223> OTHER INFORMATION: single-chain variable fragment (scFv),
      scFv_fmc63_VH-VL

<400> SEQUENCE: 37

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Gln Met Thr Gln Thr Thr Ser
    130                 135                 140

Ser Leu Ser Ala Ser Leu Gly Asp Arg Val Thr Ile Ser Cys Arg Ala
145                 150                 155                 160

Ser Gln Asp Ile Ser Lys Tyr Leu Asn Trp Tyr Gln Gln Lys Pro Asp
                165                 170                 175

Gly Thr Val Lys Leu Leu Ile Tyr His Thr Ser Arg Leu His Ser Gly
            180                 185                 190

Val Pro Ser Arg Phe Ser Gly Ser Gly Ser Gly Thr Asp Tyr Ser Leu
        195                 200                 205

Thr Ile Ser Asn Leu Glu Gln Glu Asp Ile Ala Thr Tyr Phe Cys Gln
    210                 215                 220

Gln Gly Asn Thr Leu Pro Tyr Thr Phe Gly Gly Gly Thr Lys Leu Glu
225                 230                 235                 240

Ile Thr Lys Ala

<210> SEQ ID NO 38
<211> LENGTH: 244
<212> TYPE: PRT
<213> ORGANISM: Artificial Sequence
<220> FEATURE:
<223> OTHER INFORMATION: scFv, scFv_fmc63_VL-VH

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr

```
            20                  25                  30
Leu Asn Trp Tyr Gln Gln Lys Pro Asp Gly Thr Val Lys Leu Leu Ile
         35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Lys Ala Gly Gly Gly
                100                 105                 110

Gly Ser Gly Gly Gly Ser Gly Gly Gly Ser Glu Val Lys Leu
         115                 120                 125

Gln Glu Ser Gly Pro Gly Leu Val Ala Pro Ser Gln Ser Leu Ser Val
         130                 135                 140

Thr Cys Thr Val Ser Gly Val Ser Leu Pro Asp Tyr Gly Val Ser Trp
145                 150                 155                 160

Ile Arg Gln Pro Pro Arg Lys Gly Leu Glu Trp Leu Gly Val Ile Trp
                165                 170                 175

Gly Ser Glu Thr Thr Tyr Tyr Asn Ser Ala Leu Lys Ser Arg Leu Thr
                180                 185                 190

Ile Ile Lys Asp Asn Ser Lys Ser Gln Val Phe Leu Lys Met Asn Ser
         195                 200                 205

Leu Gln Thr Asp Asp Thr Ala Ile Tyr Tyr Cys Ala Lys His Tyr Tyr
 210                 215                 220

Tyr Gly Gly Ser Tyr Ala Met Asp Tyr Trp Gly Gln Gly Thr Ser Val
225                 230                 235                 240

Thr Val Ser Ser

<210> SEQ ID NO 39
<211> LENGTH: 249
<212> TYPE: PRT
<213> ORGANISM: Artificial Sequence
<220> FEATURE:
<223> OTHER INFORMATION: scFv, scFv_4g7_VH-VL

<400> SEQUENCE: 39

Glu Val Gln Leu Gln Gln Ser Gly Pro Glu Leu Ile Lys Pro Gly Ala
 1               5                  10                  15

Ser Val Lys Met Ser Cys Lys Ala Ser Gly Tyr Thr Phe Thr Ser Tyr
                 20                  25                  30

Val Met His Trp Val Lys Gln Lys Pro Gly Gln Gly Leu Glu Trp Ile
         35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Gly Thr Tyr Tyr Gly Ser Arg Val Phe Asp Tyr Trp Gly
                100                 105                 110

Gln Gly Thr Thr Leu Thr Val Ser Ser Gly Gly Gly Ser Gly Gly
         115                 120                 125

Gly Gly Ser Gly Gly Gly Ser Asp Ile Val Met Thr Gln Ala Ala
 130                 135                 140
```

```
Pro Ser Ile Pro Val Thr Pro Gly Glu Ser Val Ser Ile Ser Cys Arg
145                 150                 155                 160

Ser Ser Lys Ser Leu Leu Asn Ser Asn Gly Asn Thr Tyr Leu Tyr Trp
                165                 170                 175

Phe Leu Gln Arg Pro Gly Gln Ser Pro Gln Leu Leu Ile Tyr Arg Met
            180                 185                 190

Ser Asn Leu Ala Ser Gly Val Pro Asp Arg Phe Ser Gly Ser Gly Ser
        195                 200                 205

Gly Thr Ala Phe Thr Leu Arg Ile Ser Arg Val Glu Ala Glu Asp Val
    210                 215                 220

Gly Val Tyr Tyr Cys Met Gln His Leu Glu Tyr Pro Phe Thr Phe Gly
225                 230                 235                 240

Ala Gly Thr Lys Leu Glu Leu Lys Arg
                245
```

<210> SEQ ID NO 40
<211> LENGTH: 250
<212> TYPE: PRT
<213> ORGANISM: Artificial Sequence
<220> FEATURE:
<223> OTHER INFORMATION: scFv, scFv_4g7_VL-VH

<400> SEQUENCE: 40

```
Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ser Gly Gly Gly Gly Ser Gly Gly Gly Gly Ser Gly Gly Gly Gly
        115                 120                 125

Ser Glu Val Gln Leu Gln Gln Ser Gly Pro Glu Leu Ile Lys Pro Gly
    130                 135                 140

Ala Ser Val Lys Met Ser Cys Lys Ala Ser Gly Tyr Thr Phe Thr Ser
145                 150                 155                 160

Tyr Val Met His Trp Val Lys Gln Lys Pro Gly Gln Gly Leu Glu Trp
                165                 170                 175

Ile Gly Tyr Ile Asn Pro Tyr Asn Asp Gly Thr Lys Tyr Asn Glu Lys
            180                 185                 190

Phe Lys Gly Lys Ala Thr Leu Thr Ser Asp Lys Ser Ser Ser Thr Ala
        195                 200                 205

Tyr Met Glu Leu Ser Ser Leu Thr Ser Glu Asp Ser Ala Val Tyr Tyr
    210                 215                 220

Cys Ala Arg Gly Thr Tyr Tyr Gly Ser Arg Val Phe Asp Tyr Trp
225                 230                 235                 240

Gly Gln Gly Thr Thr Leu Thr Val Ser Ser
                245                 250
```

```
<210> SEQ ID NO 41
<211> LENGTH: 242
<212> TYPE: PRT
<213> ORGANISM: Artificial Sequence
<220> FEATURE:
<223> OTHER INFORMATION: scFv, scFv_CAT_VL-VH

<400> SEQUENCE: 41

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Ser Tyr Phe Leu Thr Ile Asn Asn Met Glu Ala Glu
65                  70                  75                  80

Asp Ala Ala Thr Tyr Tyr Cys Gln Gln Trp Asn Ile Asn Pro Leu Thr
                85                  90                  95

Phe Gly Ala Gly Thr Lys Leu Glu Leu Lys Arg Ser Gly Gly Gly Gly
            100                 105                 110

Ser Gly Gly Gly Ser Gly Gly Gly Ser Gln Val Gln Leu Gln
            115                 120                 125

Gln Ser Gly Pro Glu Leu Val Lys Pro Gly Ala Ser Val Lys Ile Ser
        130                 135                 140

Cys Lys Ala Ser Gly Tyr Ala Phe Ser Ser Trp Met Asn Trp Val
145                 150                 155                 160

Lys Gln Arg Pro Gly Lys Gly Leu Glu Trp Ile Gly Arg Ile Tyr Pro
                165                 170                 175

Gly Asp Glu Asp Thr Asn Tyr Ser Gly Lys Phe Lys Asp Lys Ala Thr
            180                 185                 190

Leu Thr Ala Asp Lys Ser Ser Thr Thr Ala Tyr Met Gln Leu Ser Ser
        195                 200                 205

Leu Thr Ser Glu Asp Ser Ala Val Tyr Phe Cys Ala Arg Ser Leu Leu
    210                 215                 220

Tyr Gly Asp Tyr Leu Asp Tyr Trp Gly Gln Gly Thr Thr Leu Thr Val
225                 230                 235                 240

Ser Ser

<210> SEQ ID NO 42
<211> LENGTH: 494
<212> TYPE: PRT
<213> ORGANISM: Artificial Sequence
<220> FEATURE:
<223> OTHER INFORMATION: Fmc63_CAR

<400> SEQUENCE: 42

Met Glu Thr Asp Thr Leu Leu Leu Trp Val Leu Leu Leu Trp Val Pro
1               5                   10                  15

Gly Ser Thr Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60
```

-continued

```
Lys Leu Leu Ile Tyr His Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                 85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Thr Lys Leu Glu Ile Thr Lys
        115                 120                 125

Ala Gly Gly Gly Ser Gly Gly Gly Ser Gly Gly Gly Gly Ser
    130                 135                 140

Gly Gly Gly Gly Ser Glu Val Lys Leu Gln Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
            180                 185                 190

Gly Leu Glu Trp Leu Gly Val Ile Trp Gly Ser Glu Thr Thr Tyr Tyr
        195                 200                 205

Asn Ser Ala Leu Lys Ser Arg Leu Thr Ile Ile Lys Asp Asn Ser Lys
210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Gly Gly Ser Tyr Ala Met
                245                 250                 255

Asp Tyr Trp Gly Gln Gly Thr Ser Val Thr Val Ser Ser Asp Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480
```

```
Asp Thr Tyr Asp Ala Leu His Met Gln Ala Leu Pro Pro Arg
                485                 490

<210> SEQ ID NO 43
<211> LENGTH: 18
<212> TYPE: PRT
<213> ORGANISM: Artificial Sequence
<220> FEATURE:
<223> OTHER INFORMATION: Linker

<400> SEQUENCE: 43

Ser Gly Gly Gly Gly Ser Ser Gly Gly Gly Gly Ser Ser Gly Gly Gly
1               5                   10                  15

Gly Ser
```